United States Patent
Dong et al.

(10) Patent No.: US 10,444,757 B2
(45) Date of Patent: Oct. 15, 2019

(54) SELF-MOVING DEVICE AND CONTROL METHOD THEREFOR

(71) Applicant: Positec Power Tools (Suzhou) Co., Ltd., Suzhou (CN)

(72) Inventors: Yongming Dong, Suzhou (CN); Fangshi Liu, Suzhou (CN); Zhendong Gao, Suzhou (CN); Yiyun Tan, Suzhou (CN)

(73) Assignee: Positec Power Tools (Suzhou) Co., Ltd., Suzhou (CN)

( * ) Notice: Subject to any disclaimer, the term of this patent is extended or adjusted under 35 U.S.C. 154(b) by 0 days.

(21) Appl. No.: 15/551,718

(22) PCT Filed: Jan. 26, 2017

(86) PCT No.: PCT/CN2017/072748
§ 371 (c)(1),
(2) Date: Aug. 17, 2017

(87) PCT Pub. No.: WO2017/133638
PCT Pub. Date: Aug. 10, 2017

(65) Prior Publication Data
US 2018/0329420 A1   Nov. 15, 2018

(30) Foreign Application Priority Data

Feb. 3, 2016 (CN) .......................... 2016 1 0076150
Mar. 30, 2016 (CN) ..................... 2016 2 0260436 U
(Continued)

(51) Int. Cl.
*G05D 1/02* (2006.01)
*G01N 33/00* (2006.01)
(Continued)

(52) U.S. Cl.
CPC ........... *G05D 1/0219* (2013.01); *A01D 34/00* (2013.01); *A01D 34/008* (2013.01); *G01D 5/12* (2013.01);
(Continued)

(58) Field of Classification Search
USPC .......................................................... 701/23
See application file for complete search history.

(56) References Cited

U.S. PATENT DOCUMENTS 4,887,415 A   12/1989 Martin
7,441,298 B2   10/2008 Svendsen et al.
(Continued)

FOREIGN PATENT DOCUMENTS

CA          2407049 A1    12/2001
CN        101828464 A     9/2010
(Continued)

OTHER PUBLICATIONS

International Search Report for International Application No. PCT/CN2017/072748, dated May 5, 2017.

*Primary Examiner* — Tyler D Paige
(74) *Attorney, Agent, or Firm* — Middleton Reutlinger

(57) ABSTRACT

The present invention relates to a self-moving device, which moves and works in a working area defined by a limit and comprises a shell, a moving module, a task executing module and a control module; the control module controls the moving module to drive the self-moving device to move and controls the task executing module to execute a work task; the self-moving device comprising at least one capacitance sensor, which is mounted in the shell and electrically connected to the control module and detects whether a surface below the self-moving device or in front of a moving direction is a surface to be machined; the capacitance sensor comprises at least one probe, the probe comprises a probing
(Continued)

surface located on the outer surface of the probe, and a conductivity of at least part of the probing surface is larger than or equal to $10^{-9}$ s/m; or a distance between the probe and the surface below the self-moving device meets a first preset condition; or an area of the probing surface meets a second preset condition.

15 Claims, 28 Drawing Sheets

(30) Foreign Application Priority Data

Apr. 7, 2016 (CN) .......................... 2016 1 0214095
Jun. 15, 2016 (CN) .......................... 2016 1 0423176

(51) Int. Cl.
*A01D 34/00* (2006.01)
*G01D 5/12* (2006.01)
*G01N 27/22* (2006.01)
*A01D 101/00* (2006.01)

(52) U.S. Cl.
CPC ......... *G01N 27/22* (2013.01); *G01N 33/0098* (2013.01); *A01D 2101/00* (2013.01); *G05D 2201/0208* (2013.01)

(56) References Cited

U.S. PATENT DOCUMENTS

| | | | |
|---|---|---|---|
| 7,613,552 | B2 | 11/2009 | Bernini et al. |
| 7,668,631 | B2 | 2/2010 | Bernini et al. |
| 8,285,435 | B2 | 10/2012 | Bernini |
| 9,237,689 | B2 | 1/2016 | Choi et al. |
| 2002/0049521 | A1 | 4/2002 | Ruffner |
| 2003/0117321 | A1* | 6/2003 | Furse ............... H01Q 1/36 343/700 MS |
| 2004/0095149 | A1 | 5/2004 | Chen et al. |
| 2006/0005632 | A1 | 1/2006 | Chen et al. |
| 2007/0234492 | A1 | 10/2007 | Svendsen et al. |
| 2008/0003997 | A1 | 1/2008 | Parkkinen et al. |
| 2008/0039974 | A1* | 2/2008 | Sandin ............... G05D 1/0225 700/258 |
| 2008/0091305 | A1 | 4/2008 | Svendsen et al. |
| 2008/0109126 | A1 | 5/2008 | Sandin et al. |
| 2008/0282658 | A1 | 11/2008 | Bernini |
| 2009/0183478 | A1 | 7/2009 | Bernini |
| 2009/0254218 | A1 | 10/2009 | Sandin et al. |
| 2010/0326030 | A1 | 12/2010 | Bernini et al. |
| 2013/0117952 | A1 | 5/2013 | Schnittman et al. |
| 2013/0192183 | A1 | 8/2013 | Choi et al. |
| 2013/0199145 | A1 | 8/2013 | Hwang et al. |
| 2014/0102061 | A1* | 4/2014 | Sandin ............... G05D 1/0225 56/10.2 A |
| 2014/0102062 | A1 | 4/2014 | Sandin et al. |
| 2015/0006015 | A1 | 1/2015 | Sandin et al. |
| 2015/0020326 | A1 | 1/2015 | Schnittman et al. |
| 2015/0234385 | A1* | 8/2015 | Sandin ............... G05D 1/0265 700/258 |
| 2016/0057925 | A1 | 3/2016 | Letsky |
| 2016/0128275 | A1 | 5/2016 | Johnson |

FOREIGN PATENT DOCUMENTS

| | | |
|---|---|---|
| CN | 102498364 A | 6/2012 |
| CN | 102640625 A | 8/2012 |
| CN | 103196358 A | 7/2013 |
| CN | 103234460 A | 8/2013 |
| CN | 104224058 A | 12/2014 |
| CN | 205567099 U | 9/2016 |
| CN | 205611273 U | 10/2016 |
| CN | 205825980 U | 12/2016 |
| DE | 19932552 A1 | 2/2000 |
| DE | 10327223 A1 | 1/2005 |
| DE | 102015221128 A1 | 5/2016 |
| EP | 1284628 A2 | 2/2003 |
| EP | 1969437 A2 | 9/2008 |
| EP | 1992211 A1 | 11/2008 |
| EP | 1996987 A2 | 12/2008 |
| EP | 2082638 A1 | 7/2009 |
| EP | 2210466 A1 | 7/2010 |
| EP | 2281428 A1 | 2/2011 |
| EP | 3067771 A1 | 9/2016 |
| GB | 2295304 A | 5/1996 |
| GB | 2334874 A | 9/1999 |
| GB | 2334875 A | 9/1999 |
| GB | 2532592 A | 5/2016 |
| IT | 1377103 B | 7/2010 |
| IT | 1388434 B | 5/2011 |
| IT | 1395844 B1 | 10/2012 |
| JP | S61131609 A | 6/1986 |
| JP | 2009518073 A | 5/2009 |
| JP | 2011218210 A | 11/2011 |
| JP | 2014236955 A | 12/2014 |
| JP | 2016201096 A | 12/2016 |
| KP | 2008072961 | 8/2008 |
| KP | 2009005616 | 1/2009 |
| KP | 2013015458 | 2/2013 |
| KP | 2013020062 | 2/2017 |
| MY | 134306 A | 12/2007 |
| WO | WO-2007065033 A2 | 6/2007 |
| WO | WO-2007066195 A2 | 6/2007 |
| WO | WO-2007109624 A2 | 9/2007 |
| WO | WO-2016148743 A1 | 9/2016 |

* cited by examiner

SELF-MOVING DEVICE AND CONTROL METHOD THEREFOR

CROSS-REFERENCE TO RELATED APPLICATIONS

This is the United States national phase of International Patent Application No. PCT/CN2017/072748, filed Jan. 26, 2017, which claims the benefit of priority of CN 201610076150.X, filed Feb. 3, 2016; CN 201620260436.9, filed Mar. 30, 2016; CN 201610214095.6, filed Apr. 7, 2016; and CN 201610423176.7, filed Jun. 15, 2016, the entire contents of each of which being hereby incorporated herein by reference.

FIELD OF THE DISCLOSURE

The present disclosure relates to a self-moving device, and further relates to a control method for a self-moving device.

BACKGROUND

A mower is a lawn trimming tool and usually comprises a wheel set, an enclosure and a cutting system and can walk on a lawn and cut a grassland. A traditional mower mainly uses a gasoline engine or an alternating current system as a cutting power, and is pushed by manpower to walk back and forth on the lawn to finish nursing and trimming of the grassland. However, labor intensity for pushing the mower to mow grass is larger.

Along with continuous development of computer technology and artificial intelligence technology, an intelligent mower similar to an intelligent robot has slowly emerged in people's life. The intelligent mower can automatically mow and be charged in the lawn of a user without user intervention. After set once, such automatic working system needs no management any more, and the user is liberated from dull and time-consuming and labor-consuming housework such as lawn cleaning and maintenance.

Compared with the traditional mower, the intelligent mower has an automatic walking function and has a sensor with a lawn recognizing function, and the intelligent mower adopts a capacitance sensor to automatically recognize the grassland to be trimmed, and can automatically finish lawn trimming work without a need of manual direct control and operation, manual operation is greatly reduced, and the intelligent mower is a tool suitable for lawn trimming and maintenance in occasions such as family courtyards and public green spaces.

The capacitance sensor detects the ground below the mower, judges whether the ground is the grassland to be mowed and further controls a working condition of a mowing motor. However, some grassland sensors in prior art have a problem of poor sensitivity, and some noncontact grassland sensors are also easily interfered by factors such as air.

The capacitance sensor of the intelligent mower comprises a probe, configured to detect the grassland; the capacitance sensor also comprises an end cover in order to protect the probe from damage, and the end cover is disposed on the bottom of the capacitance sensor, and separates the grassland from the probe. However, for a traditional intelligent mower, the end cover on the bottom of the capacitance sensor is unfavorable for transmission of an electric field of the probe, which causes the poor sensitivity of the capacitance sensor and a poor grassland detection effect.

Another problem is that for the traditional intelligent mower, the capacitance sensor adopts a fixed columnar type, during lawn trimming and maintenance, when the intelligent mower automatically walks, the sensor easily rubs against the grassland, which increases a walking resistance of the intelligent mower and obstructs the walking of the intelligent mower.

GENERAL DESCRIPTION

In order to solve the existing technical problem, a technical solution adopted by the present invention is:

A self-moving device, moving and working in a working area defined by a limit, comprises a shell, a moving module, a task executing module and a control module;

the control module controls the moving module to drive the self-moving device to move and controls the task executing module to execute a work task;

the self-moving device comprises at least one capacitance sensor, which is mounted to the shell and electrically connected to the control module and detects whether a surface below the self-moving device or in front of a moving direction is a surface to be processed;

the capacitance sensor comprises at least one probe, the probe comprises a probing surface located on the outer surface of the probe, and a conductivity of at least part of the probing surface is larger than or equal to $10^{-9}$ s/m;

or a distance between the probe and the surface below the self-moving device meets a first preset condition;

or an area of the probing surface meets a second preset condition.

Preferably, the probing surface comprises a lower surface facing to the surface below the self-moving device, and a conductivity of the lower surface is larger than or equal to $10^{-9}$ s/m.

Preferably, the capacitance sensor comprises a longitudinal axis extending downwards from the shell, the probing surface comprises a surrounding surface around the longitudinal axis, and a conductivity of the surrounding surface is larger than or equal to $10^{-9}$ s/m.

Preferably, the probing surface comprises a side surface, vertical to a working surface of the self-moving device or inclined for a preset angle relative to the working surface of the self-moving device, and a conductivity of the side surface is larger than or equal to $10^{-9}$ s/m.

Preferably, the probe comprises at least one polar plate electrically connected to the control module, a conductivity of the polar plate is larger than or equal to $10^{-9}$ s/m, and the probing surface comprises a surface of the polar plate.

Preferably, the probe comprises at least one polar plate electrically connected to the control module and a cladding layer at least partially cladding the polar plate, a conductivity of an outer surface of the cladding layer is larger than or equal to $10^{-9}$ s/m, and the probing surface comprises an outer surface of the cladding layer.

Preferably, the cladding layer comprises an inner layer close to the polar plate and an outer layer away from the polar plate, a conductivity of the inner layer is smaller than or equal to $10^{-9}$ s/m, and a conductivity of the outer layer is larger than or equal to $10^{-9}$ s/m.

Preferably, an interval between the polar plate and the outer layer of the cladding layer is smaller than or equal to a preset distance.

Preferably, the control module comprises a signal processing circuit processing an electric signal input by the capacitance sensor and also comprises a protective circuit electrically connected to the capacitance sensor and the signal processing circuit, and when a value of the electric value input by the capacitance sensor is larger than or equal to a threshold, the protective circuit reduces the value of the electric value input by the capacitance sensor, so that the value of the electric value input to the signal processing circuit is kept in a preset range.

Preferably, the first preset condition is that a distance between the probe and the surface below the self-moving device is smaller than a distance between a tail end of the task executing module and the surface below the self-moving device.

Preferably, the first preset condition is that a distance between the probe and the surface below the self-moving device is smaller than a height of a medium on a working plane of the self-moving device.

Preferably, the first preset condition is that a distance between the probe and the surface below the self-moving device is smaller than or equal to 50 mm.

Preferably, the first preset condition is that a distance between the probe and the surface below the self-moving device is larger than or equal to 10 mm.

Preferably, the capacitance sensor comprises a connecting part connected to probe and the shell, and the connecting part can drive the probe to move relative to the shell.

Preferably, the connecting part can drive the probe to move in a height direction relative to the shell.

Preferably, the connecting part can drive the probe to swing in a horizontal direction relative to the shell.

Preferably, the connecting part is made of a flexible material.

Preferably, the capacitance sensor comprises a longitudinal axis extending downwards from the bottom of the shell, and the connecting part comprises a through hole along the longitudinal axis for a lead, electrically connected to the probe and the control module, to penetrate through.

Preferably, the second preset condition is that an area of the probing surface is larger than or equal to 28 $cm^2$.

Preferably, the probe comprises at least one polar plate electrically connected to the control module, and an area of the polar plate is larger than or equal to 28 $cm^2$.

Preferably, the probe comprises a concavo-convex surface, and the probing surface comprises the concavo-convex surface.

Preferably, the probe comprises a plurality of teeth, and the probing surface comprises surfaces of the teeth.

Preferably, at least one of the capacitance sensors is disposed at the front end or back end of the shell.

Preferably, the moving module comprises a front wheel and a back wheel, and at least one of the capacitance sensors is disposed at the front side of the front wheel or the back side of the back wheel.

Preferably, the moving module comprises a front wheel and a back wheel, and at least one of the capacitance sensors is disposed between the front side of the front wheel and the back side of the back wheel.

Preferably, at least two groups of capacitance sensors are included and are respectively disposed on both sides of the shell.

Preferably, the probe comprises at least two polar plates electrically connected to the control module respectively, and the polar plates have different potentials.

Preferably, the polar plate comprises a shielding side back to the surface below the self-moving device, and the shielding side is provided with a shielding layer.

Preferably, the capacitance sensor comprises a connecting part connected to the probe and the shell, the probe comprises a first rotary shaft parallel with a working surface of the self-moving device, and the probe can rotate around the first rotary shaft relative to the connecting part.

Preferably, the connecting part comprises a second rotary shaft vertical to the working surface of the self-moving device, and the connecting part can rotate around the second rotary shaft relative to the shell, so that the probe rotates around the second rotary shaft.

Preferably, the probe is a wheel, and the first rotary shaft is a wheel axle of the wheel.

Preferably, the bottom of the idler wheel is higher than the bottom of the moving module.

A control method for a self-moving device is provided, where the self-moving device comprises at least one capacitance sensor for detecting whether a surface below the self-moving device or in front of a moving direction is a surface to be processed, the capacitance sensor comprises at least one probe, the probe comprises a probing surface located on the outer surface of the probe, and the control method for a self-moving device comprises the following steps:

providing the probing surface, part of which has a conductivity being larger than or equal to $10^{-9}$ s/m, or providing the probe, a distance between which and the surface below the self-moving device meets a first preset condition, or providing the probing surface of which an area meets a second preset condition;

judging whether the surface below the self-moving device or in front of a moving direction is a surface to be machined according to an electric signal output by the capacitance sensor;

if yes, controlling the self-moving device to continuously move; and if not, controlling the self-moving device to change a moving manner.

A capacitance sensor comprises a metal polar plate and an end cover; the end cover is disposed outside the metal polar plate and configured to protect the metal polar plate; the capacitance sensor also comprises an insulating interlayer, disposed between the metal polar plate and the end cover; and the end cover is made of a conductive material.

When the capacitance sensor works, the metal polar plate will transmit an electric field to a to-be-detected article to detect the to-be-detected article. Since the end cover is a conductor with high conductivity, the end cover is favorable for transmission of the electric field of the metal polar plate, and sensitivity of the capacitance sensor is effectively enhanced, so that the a detection effect of the metal polar plate of the capacitance sensor is better.

In one of the embodiments, the insulating interlayer is made of a plastic or a rubber material.

In one of the embodiments, the end cover is a metal end cover.

In one of the embodiments, the metal polar plate is a metal thin plate; the capacitance sensor also comprises a base plate, the end cover is disposed on one side of the metal polar plate, the base plate is disposed on the other side of the metal polar plate, the metal polar plate is embedded on the base plate, and the base plate is configured to fix the metal polar plate.

In one of the embodiments, the capacitance sensor also comprises a lead and a fixing structure, and the lead penetrates through the base plate to be connected to the metal polar plate; the fixing structure surrounds the lead, the fixing structures abuts against the base plate and the fixing structure is configured to fix the lead.

In one of the embodiments, the fixing structure is made of a sponge material.

In one of the embodiments, the capacitance sensor also comprises a sensor shell which is cylindrical, the side wall of the sensor shell defines an inner cavity, the fixing structure and the base plate are disposed in the inner cavity, the base plate is vertical to a central axis of the sensor shell, the fixing structure and the base plate abut against the side wall of the sensor shell, the side wall of the sensor shell and the end cover are connected together in a matching manner, and the sensor shell, the fixing structure and the end cover are matched together to protect the metal polar plate.

In one of the embodiments, the side wall of the sensor shell is connected to the end cover through screws.

In one of the embodiments, the end cover comprises a flange, the flange is disposed on one side of the end cover facing to the shell, the flange surrounds the side wall of the sensor shell, and the flange is connected to the side wall of the sensor shell through threads.

A mower comprises a controller, a signal processing circuit and the capacitance sensor according to any one of the embodiments above; the capacitance sensor comprises a metal polar plate and an end cover, the end cover is disposed outside the metal polar plate and the end cover is made of a conductive material; an input end of the signal processing circuit is connected to the metal polar plate; and an input end of the controller is connected to an output end of the signal processing circuit.

The mower above is configured to cut vegetation. When the capacitance sensor works, the metal polar plate will transmit an electric field to the vegetation to detect the vegetation. The end cover is located between the metal polar plate and the vegetation, since the end cover is made of a conductive material, the conductivity is high, the end cover is favorable for transmission of the electric field of the metal polar plate, and a sensitivity of the capacitance sensor is effectively enhanced, such that the metal polar plate of the capacitance sensor has a better vegetation detection effect. The metal polar plate transmits a signal of the detected vegetation to a processor through the signal processing circuit, and the mower can executing a work task according to the vegetation detection condition of the metal polar plate, so that the effect of vegetation cutting is better.

A mower is configured to cut vegetation on a working surface, the mower comprises a shell and a sensing component; the sensing component is disposed on the shell, the sensing component comprises a sensor, a height of the sensor relative to the working surface is adjustable, and the sensor is configured to sense the vegetation.

According to the mower above, since the height of the sensor relative to the working surface is adjustable, so that a user can adjust the height of the sensor according to the height of the vegetation, when the vegetation is lower, the height of the sensor is reduced, then the mower can recognize the vegetation without misjudgment, so that a mowing cutterhead is started to cut the vegetation, the vegetation that should be trimmed will not be omitted, a cutting effect is better and cutting efficiency is higher.

In one of the embodiments, the mower also comprises a rotary component which can rotate and has a first side wall vertical to the working surface, and rotary teeth are disposed on the surface of the first side wall; the sensing component has a second side wall vertical to the working surface, the second side wall is provided with rotary threads relative to the surface of the first side wall, the rotary threads and the rotary teeth are meshed, the sensor is disposed on the second side wall, and the sensing component moves relative to the working surface along with rotation of the rotary component.

The rotary component is rotatable, the rotary teeth on the surface of the first side wall are meshed with the rotary threads on the surface of the second side wall, when the rotary component rotates, the rotary teeth rotate around the rotary threads, a height of the rotary component is unchanged, and therefore, the rotary component drives the sensing component to move relative to the working surface, and further the sensor moves relative to the working surface.

In one of the embodiments, the mower further comprises a height adjusting motor, having a first output shaft, the rotary component is disposed on the first output shaft, and the height adjusting motor drives the rotary component to rotate through the first output shaft.

In one of the embodiments, the mower further comprises an adjusting component, disposed at one side of the rotary component away from the working surface, the adjusting component comprises an adjusting knob and a locking structure, where the adjusting knob can rotate and can move relative to the working surface, the locking structure is disposed between the adjusting knob and the rotary component and can rotate along with rotation of the adjusting knob, and when the adjusting knob is pressed down, the locking structure is configured to fixedly connect to the rotary component.

Thus, when the adjusting component is pressed down, the rotary component and the adjusting knob are fixedly connected together through the locking structure to realize movement of the sensing component relative to the working surface.

In one of the embodiments, the sensing component comprises a sensor connecting rod, the sensor is disposed on the sensor connecting rod, and the sensor and the sensor connecting rod are in threaded connection.

Thus, replacement of the sensor and adjustment of a relative height of the sensor relative to the sensor connecting rod are facilitated.

In one of the embodiments, one or more sensors are disposed.

Thus, a range of vegetation that can be recognized by the mower is expanded, and working efficiency of the mower is improved.

In one of the embodiments, the mower also comprises a cutting motor, located at one side of the cutting cutterhead away from the working surface, and the cutting motor provides power for the cutting cutterhead.

In one of the embodiments, the mower also comprises a motor box, the motor box sleeves outside the cutting motor and is located at one side of the cutting cutterhead away from the working surface, and the second side wall is a side wall of the motor box.

Thus, the motor box gives an enough working space for the cutting motor, such that the cutting motor does not interfere with other components when in work, in addition, the side wall of the motor box serves as the second side wall of the sensing component, the two are integrated, a weight of the cutting motor is reduced and a space occupied by components of the mower is reduced.

In one of the embodiments, the cutting motor has an output shaft capable of rotating, the cutting cutterhead is fixedly connected on the output shaft, and the cutting cutterhead rotates along with rotation of the output shaft.

Thus, after started, the cutting motor can drive the cutting cutterhead to work through the output shaft, so that the cutting cutterhead executes a cutting work.

In one of the embodiments, the rotary component and the cutting cutterhead rotate around the same axis.

In one of the embodiments, the mower also comprises a walking component, the walking component comprises at least one wheel, and the sensor is located in front of or behind a walking direction of the walking component.

In one of the embodiments, the mower also comprises a cam motor and a cam, the cam motor is fixed on the mower body, an output shaft of the cam motor is connected to a rotary shaft of the cam, the rotary shaft of the cam is parallel with the working surface, the cam comprises a projecting part facing to the working surface, and the projecting part can swing around the rotary shaft of the cam in a reciprocated manner; the sensing component also comprises a first elastic structure and a connecting rod, the first elastic structure is vertical to the working surface and comprises a fixing end and a movable end, the fixing end is fixed on the mower body, the movable end moves up and down relative to the working surface, the connecting rod is vertical to the working surface, the middle of the connecting rod is connected to the movable end, one end of the connecting rod is connected to the sensor, the other end of the connecting rod abuts against the projecting part, the reciprocated swing of the projecting part drives the connecting rod to move up and down relative to the working surface, and the first elastic structure is configured to limit the sensing component in a preset range.

In one of the embodiments, the mower also comprises a second elastic structure, and the sensing component is connected to the second elastic structure through the mower body.

In one of the embodiments, the mower also comprises a fixing plate, the fixing plate is fixed on the mower body and is provided with a through hole vertical to the working surface, and the fixing plate is configured to dispose the sensing component; the sensing component also comprises a movable rod and a limiting block, the movable rod penetrates through the through hole, the movable rod reciprocates in the through hole relative to the working surface, the limiting block is disposed at one end of the movable rod away from the working surface, the sensor is disposed at the other end of the movable rod, and the limiting block and the sensor limit the movable rod on the fixing plate.

In one of the embodiments, the sensor is a capacitance sensor including a detecting electrode, the detecting electrode is configured to sensor vegetation and a height of the detecting electrode relative to the working surface is adjustable.

In one of the embodiments, the mower also comprises a cutting cutterhead disposed on the mower body, a height of the cutting cutterhead relative to the working surface is adjustable, and the cutting cutterhead is configured to cut vegetation.

A control method for a height of a sensor is used for controlling a height of a sensor based on the mower according to any one of the embodiments above and is characterized by including the steps:

setting an initial height of the sensor, the sensor outputting an initial signal; and comparing a parameter value of the initial signal with a preset threshold, judging whether the sensor detects vegetation according to a compared result, if yes, enabling the mower to cut the vegetation or continuously walk, and if not, adjusting the sensor downwards for a specific distance.

According to the control method for a height of a sensor, the mower can judge whether the sensor detects the vegetation according to an output signal of the sensor, and the mower can adjust the height of the sensor according to a detecting condition. When the sensor detects the vegetation, the mower executes an operation of cutting the vegetation or continuously walks; and when the sensor displays that no vegetation is detected, the mower reduces the height of the sensor and continues to detect. Thus, when recognizing the vegetation, the mower will not misjudge because of short grass, accuracy of vegetation recognition is improved, a cutting effect is better and cutting efficiency is higher.

In one of the embodiments, the steps, after adjusting the sensor downwards for a specific distance, further include:

comparing a parameter value of a signal of the sensor and the parameter threshold, judging whether the sensor detects the vegetation according to a compared result, if yes, enabling the mower to cut the vegetation or continuously walk, and if not, adjusting the sensor downwards for a specific distance and outputting a height value of the sensor; and judging whether a height value of the sensor is smaller than or equal to a height threshold, if yes, indicating that the mower walks to a vegetation region and if not, adjusting the sensor downwards for a specific distance.

In one of the embodiments, the step of comparing a parameter value of the initial value with the parameter threshold, judging whether the sensor detects the vegetation according to a compared result, if yes, enabling the mower to cut the vegetation or continuously walk, and if not, adjusting the sensor downwards for a specific distance comprises: comparing a frequency value of the initial signal and a preset frequency threshold, judging whether the frequency value of the initial signal is smaller than the frequency threshold, if yes, indicating that the sensor detects the vegetation, and if not, indicating that the sensor does not detect the vegetation.

In one of the embodiments, the step of comparing a parameter value of a signal of the sensor and the parameter threshold, judging whether the sensor detects the vegetation according to a comparing result, if yes, enabling the mower to cut the vegetation or continuously walk, and if not, adjusting the sensor downwards for a specific distance and outputting a height value of the sensor comprises comparing a frequency value of a signal of the sensor and a preset frequency threshold, judging whether a frequency value of a signal of the sensor is smaller than the frequency threshold, if yes, indicating that the sensor detects the vegetation, and if not, indicating that the sensor does not detect the vegetation.

A mower comprises a shell, a cutting module, a moving module and a control module which is configured to control working of the cutting module and further comprises:

a sensor, including a first polar plate and a second polar plate;

a signal processing circuit, having an input end and an output end, wherein the input end is connected to the sensor, and the output end is connected to the control device; and the control module sends a control command to the cutting module according to a capacitance value change between a first polar plate and a second polar plate detected by the signal processing circuit.

According to the mower above, an electric field pressed to a grassland can be formed between the first polar plate and the second polar plate on the sensor, and a height change can be timely detected when the height of the grassland is changed, so as to enhance the sensitivity.

In one of the embodiments, the first polar plate and the second polar plate are located on the same horizontal plane.

In one of the embodiments, the first polar plate and the second polar plate are both disposed along a horizontal direction.

In one of the embodiments, one or more sensors are disposed and jointly form a sensing region in a width direction of the mower, and a width of the sensing region is larger than or equal to a cutting diameter of a cutting mechanism.

In one of the embodiments, when judging that a grass height is larger than a preset height according to the capacitance change, the control module controls the cutting module to execute a cutting operation.

In one of the embodiments, the first polar plate is connected to an input end of the signal processing circuit, and the second polar plate is connected to a common grounding end of the signal processing circuit; or the first polar plate is connected to a common grounding end of the signal processing circuit, and the second polar plate is connected to an input end of the signal processing circuit.

In one of the embodiments, the signal processing circuit comprises a schmitt trigger, and the first polar plate or second polar plate is connected to an input end of the schmitt trigger.

In one of the embodiments, two first polar plates are disposed, are respectively located on both sides of the second polar plate, and are connected by a lead; or one first polar plate and one second polar plate are disposed respectively, and are disposed in parallel.

In one of the embodiments, one side of the first polar plate and the second polar plate back to the grassland is provided with a shielding plate, and the shielding plate and the second polar plate are connected by a voltage follower.

In one of the embodiments, an insulation isolating plate is disposed between the first polar plate and the second polar plate and the shielding plate, and a passage for disposing the voltage follower is disposed in the insulation isolating plate.

In one of the embodiments, the sensor is mounted on the shell, and a height on the shell is adjustable.

In one of the embodiments, the sensor further comprises a support plate connected to the shell, and the first polar plate and the second polar plate are disposed on the support plate in parallel.

In one of the embodiments, the sensors are disposed at both sides of the cutting module.

In one of the embodiments, the control module is further configured to control the moving module and sends a control command to the moving module according to a capacitance value change between a first polar plate and a second polar plate detected by the signal processing circuit.

A mower comprises a shell and a sensor module which is disposed on the shell, and also comprises an idler wheel, the idler wheel is close to the bottom of the shell and is disposed at the bottom or periphery of the shell; and the sensor module comprises at least one probe which is disposed on the idler wheel and configured to sense the grassland.

According to the mower above, since the probe is disposed on the idler wheel, if the idler wheel makes a contact with the grassland, when the mower advances, the idler wheel rotates to walk, friction between the idler wheel and the grassland is converted into rolling friction, and the friction between the probe and the grassland is reduced, such that an advancing resistance of the mower is reduced, energy consumption of the mower is reduced and mowing efficiency is improved.

In one of the embodiments, the idler wheel is of a dual-layer structure, including an inner layer and an outer layer, the inner layer is provided with the probe and the outer layer is a protective layer.

In one of the embodiments, the inner layer is a metal layer, which serves as the probe.

In one of the embodiments, the outer layer is made of plastic.

In one of the embodiments, the idler wheel is suspended on the bottom of the shell.

In one of the embodiments, the idler wheel is a universal wheel.

In one of the embodiments, a bearing and a connecting are also included, the bearing is disposed on the shell, and a central axis of the bearing is vertical to the bottom of the shell; one end of the connecting shaft is connected to the bearing, and the other end is connected to the idler wheel, and the idler wheel and the connecting shaft can rotate around the central axis of the bearing.

In one of the embodiments, the mower also comprises a control module, disposed on the shell; the sensor module also comprises a signal processing circuit, an input end of the signal processing circuit is electrically connected to the probe, and an output end of the signal processing circuit is electrically connected to an input end of the control module.

In one of the embodiments, the signal processing circuit comprises a schmitt trigger, an input end of the schmitt trigger is connected to the probe, and an output end of the schmitt trigger is connected to an input end of the control module.

In one of the embodiments, the sensor module is a capacitance sensor, and the probe is a pole piece of the capacitance sensor.

In one of the embodiments, at least one main walking wheel is also included, the main walking wheel is disposed on the bottom of the shell, and the idler wheel is disposed in front of and/or behind an advancing direction of the main walking wheel.

Compared with prior art, the present invention has the beneficial effects of improving the sensitivity of the capacitance sensor, enabling judgment of the automatic mower on existence of the grassland to be more accurate and ensuring working safety of the automatic mower.

BRIEF DESCRIPTION OF THE DRAWINGS

Objectives, technical solutions and beneficial effects above of the present invention can be implemented through the following drawings.

DETAILED DESCRIPTION

Figure 1:
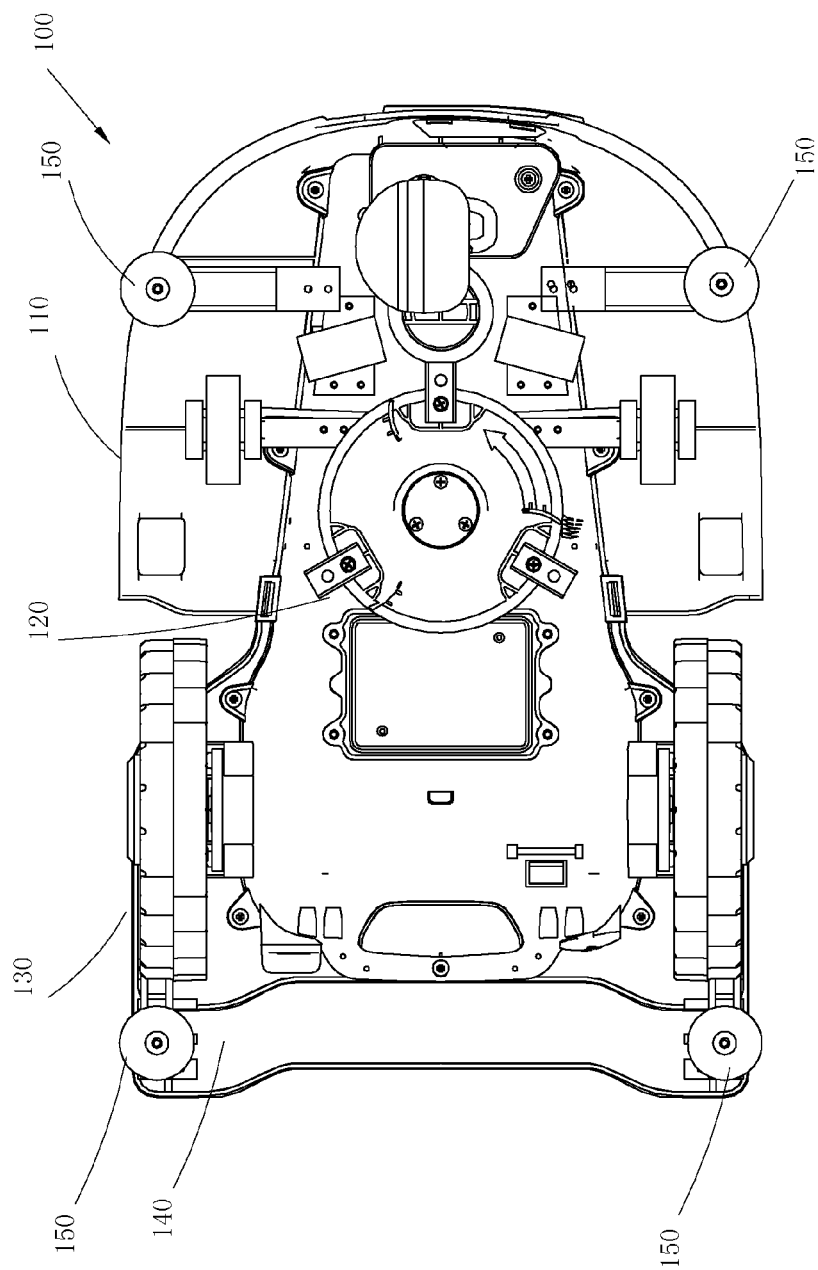
FIG. 1 is a structural schematic diagram of an automatic mower of a first embodiment of the present invention.

FIG. 1 is a structural schematic diagram of a self-moving device of a first embodiment of the present invention. A direction parallel with a working plane of the self-moving device is a horizontal direction, and a direction vertical to the working surface of the self-moving device is a height direction. In the present embodiment, the self-moving device is an automatic mower 100, and in other embodiments, the self-moving device can be suitable unattended devices such as an automatic snow sweeper and an automatic dust collector. FIG. 1 is a bottom view of the automatic mower 100, that is, a structural diagram of the automatic mower 100 saw from a position below the automatic mower 100. As shown in FIG. 1, the automatic mower 100 comprises a shell 110, a moving module 130, a task executing module, an energy module and a control module, and the moving module 130, the task executing module, the energy module and the control module are mounted to the shell 110. The shell 110 comprises a front end and a back end along a moving direction of the automatic mower 100. The moving module 130 comprises a wheel set, driven by a driving motor to drive the automatic mower 100 to move, and the wheel set comprises a front wheel and a back wheel. The task executing module is a cutting module 120 and comprises a cutting component which comprises a blade and is mounted on the bottom of the shell 110, and is driven by the cutting motor to rotate and execute mowing work. The energy module comprises a battery pack, supplying power for moving and working of the automatic mower 100. The control module is electrically connected to the moving module 130, the cutting module 120 and the energy module, the moving module 130 is controlled to drive the automatic mower 100 to move, and the cutting module 120 is controlled to execute a mowing task.

In the present embodiment, the automatic mower 100 moves and works in a working area defined by a limit (not shown). The automatic mower 100 comprises a limit detecting module, which detects a location relationship of the automatic mower 100 relative to the limit. The limit comprises limit between a grassland and a non-grassland, and when the control module judges that the automatic mower 100 is moved to the non-grassland from the grassland, the control module controls the moving module 130 to drive the automatic mower 100 to move back or steer toward the grassland. In the present embodiment, the limit detecting module comprises at least one capacitance sensor 150 which is mounted on the bottom of the shell 140 and electrically connected to the control module and detects whether the surface below or in front of a moving direction of the automatic mower 100 is a grassland to be cut.

Figure 2:
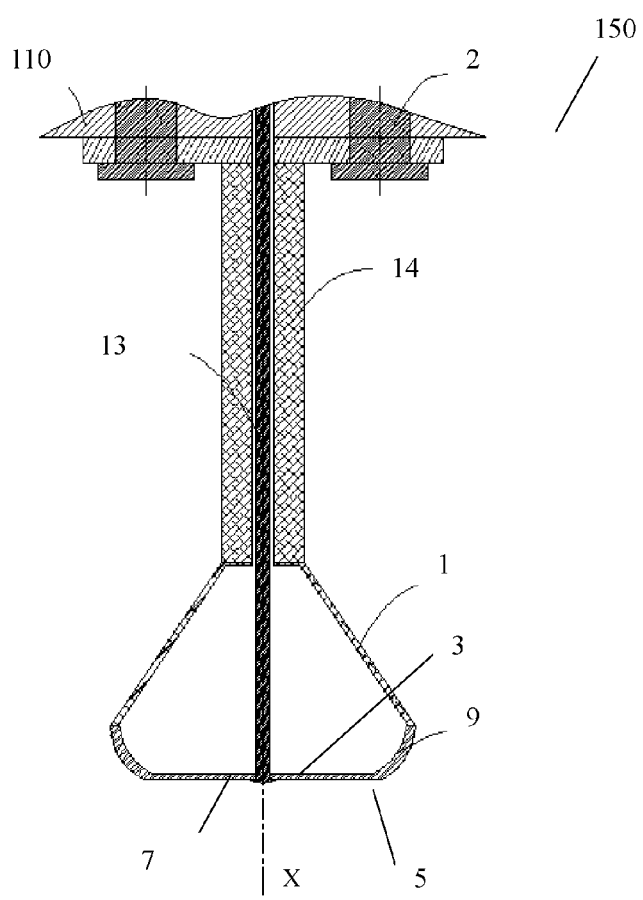
FIG. 2 is a structural schematic diagram of a capacitance sensor of a first embodiment of the present invention.

FIG. 2 is a structural schematic diagram of a capacitance sensor 150 of the present embodiment, and as shown in FIG. 2, the capacitance sensor 150 comprises a probe 1. The probe 1 comprises a probing surface 5 located on the outer surface of the probe 1, and a conductivity of at least part of the probing surface 5 is larger than or equal to $10^{-9}$ s/m. In the present embodiment, the probe 1 comprises a polar plate 3 electrically connected to the control module, and the conductivity of the polar plate 3 is larger than or equal to $10^{-9}$ s/m. In the present embodiment, the probing surface comprises a surface of the polar plate 3.

In the present embodiment, the probing surface 5 comprises a lower surface 7, facing to the surface below the automatic mower 100. The capacitance sensor 150 comprises a longitudinal axis X, downwards extending from the bottom of the shell 110, and the probing surface 5 also comprises a surrounding surface 9 surrounding the longitudinal axis X.

Figure 3A:
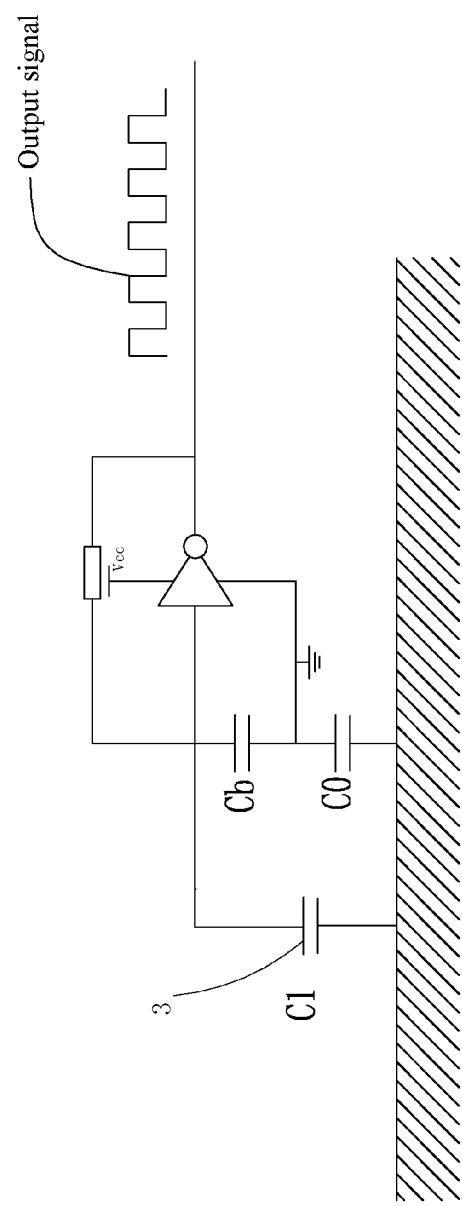
FIGS. 3(a) and 3(b) are detection principle diagrams of a capacitance sensor of a first embodiment of the present invention.
Figure 3B:
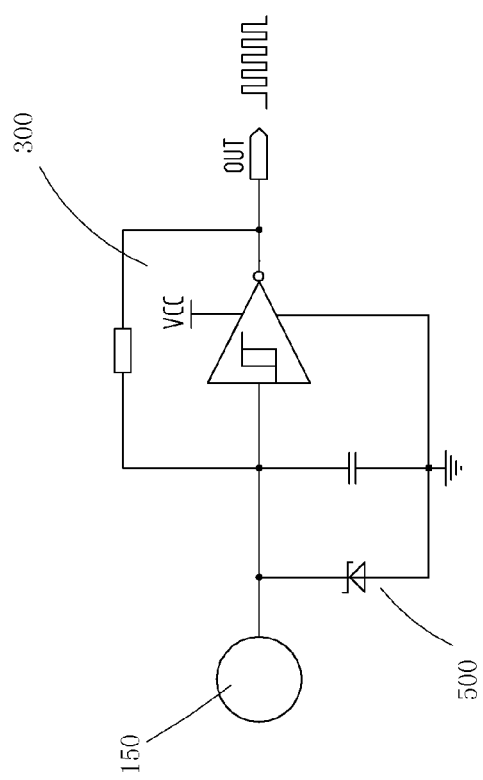

FIGS. 3(a) and 3(b) are detection principle diagrams of the capacitance sensor 150. As shown in FIG. 3(a), when the automatic mower 100 works, a capacitance C1 is formed between the probe 1 and a surface (ground surface) below the automatic mower 100. An electric signal output by the capacitance sensor 150 is related to a medium between two poles of the capacitance C1. When the surface below the probe 1 is non-grassland and the surface below the probe 1 is the grassland, the medium between the two poles is different, and the electric signal output by the capacitance sensor 150 is different. Thus, the control module can judge whether the surface below the probe 1 is the grassland according to different electric signals output by the capacitance sensor 150. Specifically, in the present embodiment, the output end of the capacitance sensor 150 is connected to an inverter of which two ends have different potentials, when a level of one end of the inverter close to the capacitance sensor 150 is higher than that of the other end, the capacitance sensor 150 discharges, when a level of one end of the inverter close to the capacitance sensor 150 is lower than that of the other end, the capacitance sensor 150 is charged, such that a charging and discharging cycle is formed in the circuit and the capacitance sensor 150 outputs a square wave signal as shown in FIG. 3(*a*). When the surface below the probe 1 is the grassland, and when the surface below the probe 1 is non-grassland, the charging and discharging rates of the capacitance sensor 150 are different, therefore, the output square waves have different frequencies, thus, the control module can judge whether the surface below the probe 1 is the grassland by detecting the frequency of square waves output by the capacitance sensor 150.

In the circuit as shown in FIG. 3(*a*), Cb is a basic capacitance disposed in the circuit, and C0 is a capacitance between the ground of a circuit board and the ground surface.

The higher the sensitivity of the capacitance sensor 150 is, the more accurate the judgment of the control module 1 on the existence of the grassland below the probe 1 is, and more reliable the control over the automatic mower 100 is. In the present embodiment, by increasing the conductivity of the probing surface 5, the sensitivity of the capacitance sensor 150 can be improved. Specifically, the polar plate 3 electrically connected to the control module is directly exposed as the probing surface 5, the conductivity of the polar plate 3 is larger than or equal to $10^{-9}$ s/m, preferably, the polar plate 3 is a conductor or semiconductor, and further, the polar plate 3 is a metal polar plate. The metal polar plate is directly exposed, reduction of the sensitivity of the capacitance sensor 150 caused by a fact that the metal polar plate is covered by the shell 110 or other structures is avoided, such that the detection accuracy of the automatic mower 100 on the limit between the grassland and the non-grassland is ensured and reliability of the automatic mower 100 is improved.

It is understandable that the metal polar plate can only be partially exposed.

In the present embodiment, since the metal polar plate of the capacitance sensor 150 is exposed outside, when the metal polar plate has higher voltage, for example, hands of people make a contact with the metal polar plate to cause static electricity, the circuit may be damaged. As shown in FIG. 3(*b*), in the present embodiment, the control module comprises a signal processing module 300 processing an electric signal input by the capacitance sensor 150, and also comprises a protective circuit 500 electrically connected to the capacitance sensor 150 and the signal processing circuit 300, and when a value of the electric signal input by the capacitance sensor 150 is larger than or equal to a threshold, the protective circuit 500 reduces the value of the electric signal input by the capacitance sensor 150, such that value of the electric signal output to the signal processing circuit 300 is kept in a preset range. Specifically, as shown in FIG. 3, in the present embodiment, the protective circuit 500 comprises an ESD protective device, when the value of the electric signal input by the capacitance sensor 150 is larger than or equal to the threshold, a diode of the protective circuit 500 is switched on and plays a role of shunting, thus, a current input into the signal processing circuit 300 is limited in a safe preset range without damaging the circuit, and working stability of the automatic mower 100 is ensured. Of course, the protective circuit 500 can directly adopt an integrated ESD protective device.

Figure 4A:
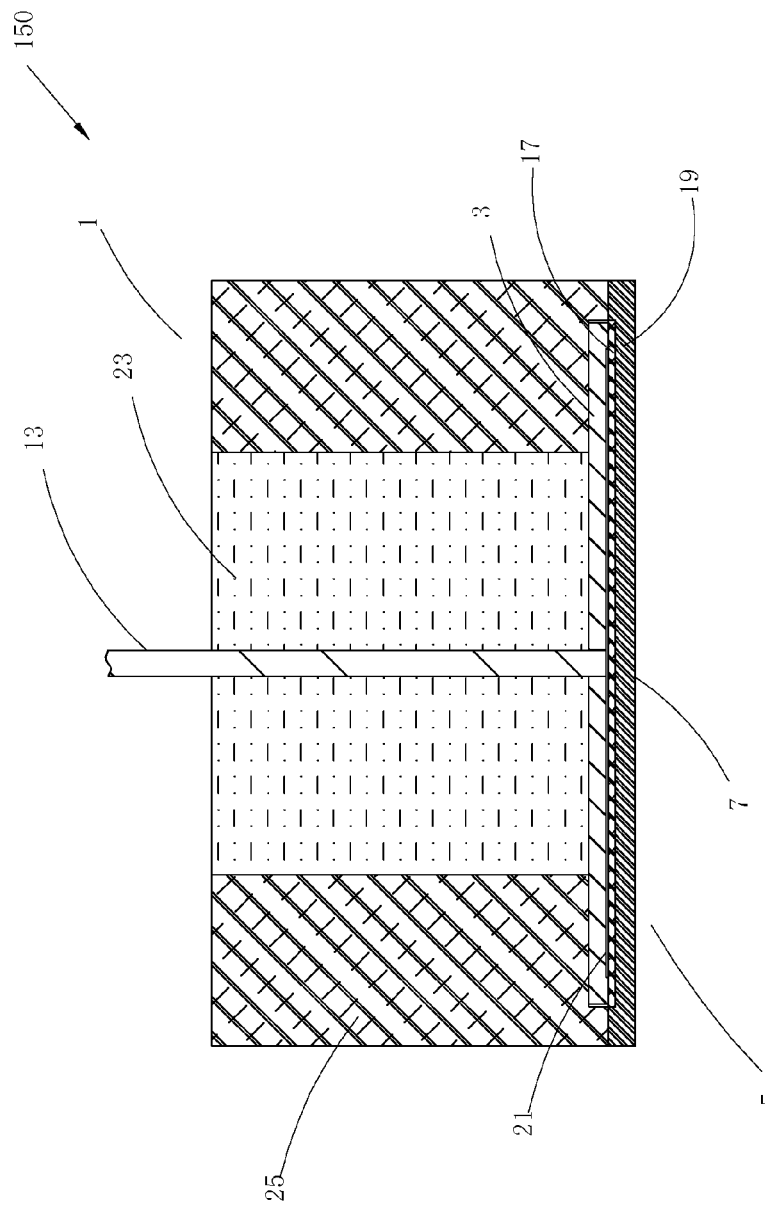
FIGS. 4(a) and 4(b) are structural schematic diagrams of a capacitance sensor of a second embodiment of the present invention.
Figure 4B:
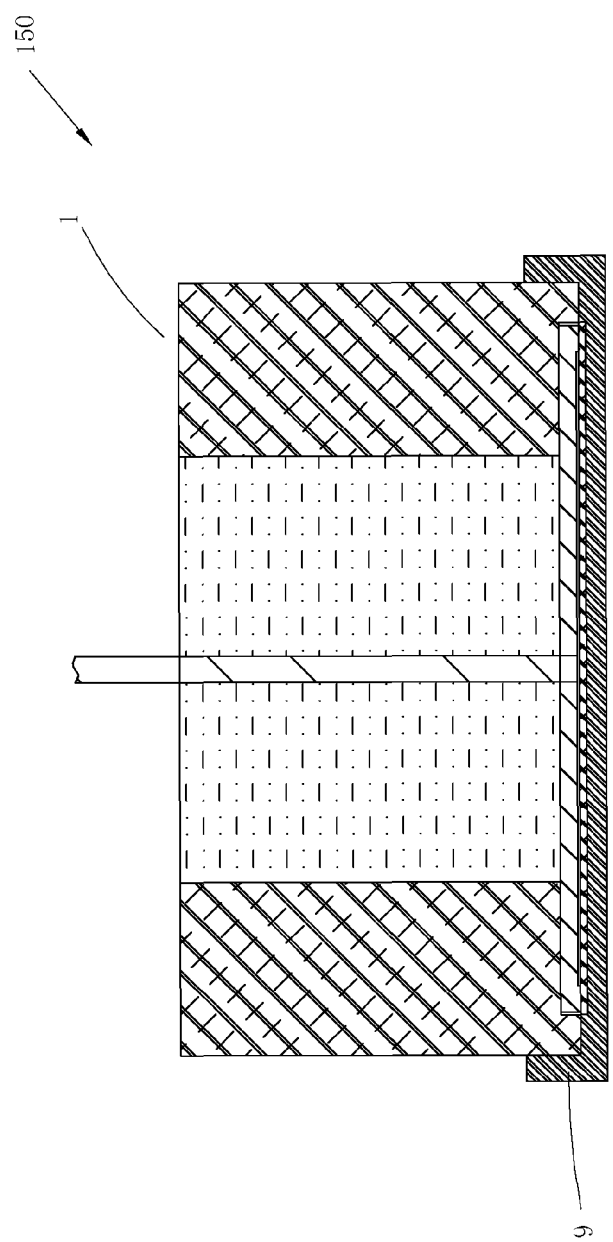
Figure 4C:
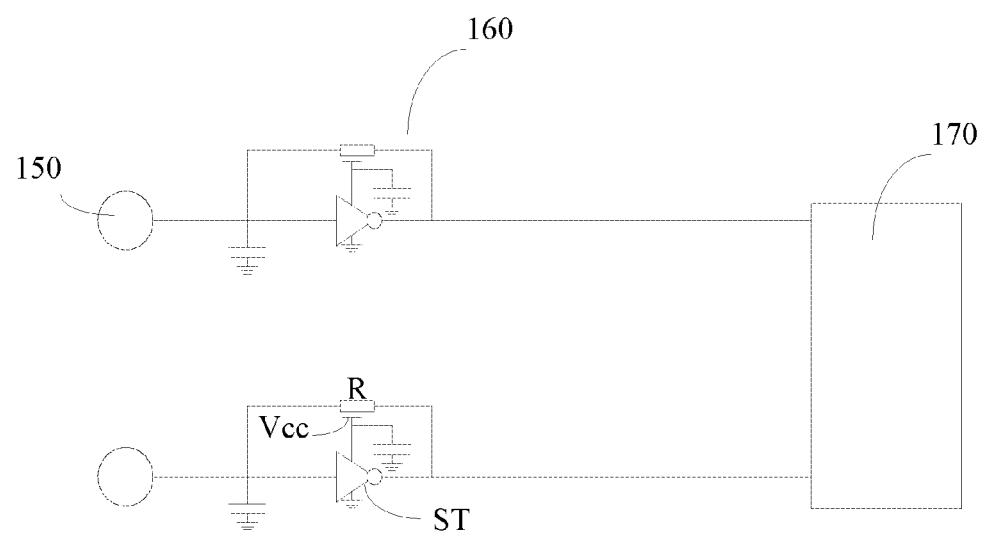
FIG. 4(c) and FIG. 5 are detection principle diagrams of a capacitance sensor of a second embodiment of the present invention.

In a second embodiment of the present invention, the structure of the probe 1 is as shown in FIG. 4(*a*) or 4(*b*), the probe comprises a polar plate 3, electrically connected to the control module and a cladding layer cladding an outer surface of the polar plate 3, a conductivity of an outer surface of the cladding layer is larger than or equal to $10^{-9}$ s/m, and the probing surface comprises the outer surface of the cladding layer. Specifically, the cladding layer comprises an inner layer 17 close to the polar plate and an outer layer 19 away from the polar plate, a conductivity of the inner layer 17 is smaller than or equal to $10^{-9}$ s/m, and a conductivity of the outer layer 19 is larger than or equal to $10^{-9}$ s/m. In the present embodiment, the polar plate 3 is a metal polar plate, the inner layer 17 of the cladding layer is an insulator (called as insulating interlayer hereinafter), the outer layer 19 of the cladding layer is a conductor or semiconductor, and specifically, the outer layer 19 of the cladding layer is metal (also called as a metal end cover hereinafter).

Figure 5:
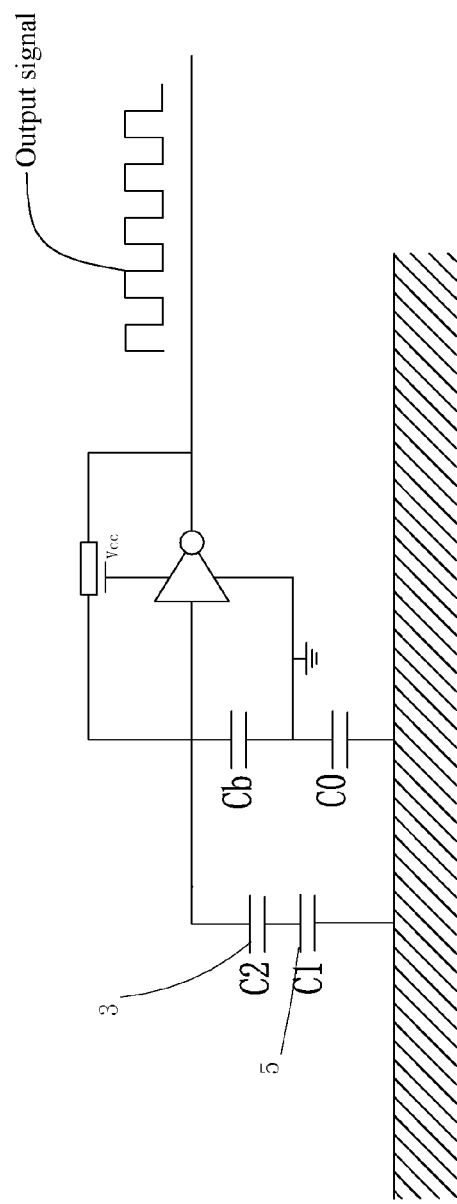

In the present embodiment, a detection principle of the capacitance sensor 150 is as shown in FIG. 5. A capacitance C1 is formed between the probing surface 5, i.e., the outer surface of the cladding layer and the ground surface. In the present embodiment, when the surface below the probe 1 is non-grassland, and when the surface below the probe 1 is grassland, the charging and discharging rates of the capacitance C1 are different, therefore, the electric signals output by the capacitance sensor 150 are different, and the control module can judge whether the surface below the probe 1 is the grassland according to different electric signal output by the capacitance sensor 150.

In the present embodiment, the cladding layer clads the outer side of the metal polar plate and comprises an insulating interlayer, which can isolate the metal polar plate from the outside and plays a role of protecting an internal circuit. In the other aspect, the outer surface of the cladding layer is metal, such that the probing surface 5 has higher conductivity, and it is ensured that the capacitance sensor 150 has higher sensitivity.

As shown in FIG. 5, in the present embodiment, a capacitance C2 is formed between the metal polar plate and the metal outer layer of the cladding layer, and the capacitances C1 and C2 are serially connected. The sensitivity of the capacitance sensor 150 in the first embodiment is higher. In the other aspect, compared with a traditional structure that only the insulating interlayer (not shown) clads the outer side of the metal polar plate, in the present embodiment, since the metal outer layer is added, sensitivity of the capacitance sensor is improved, and an influence of cladding the metal polar plate on the sensitivity of the capacitance sensor 150 is reduced.

In the present embodiment, as shown in FIG. 4(*a*), the probing surface 5 only comprises a lower surface 7 which faces to the ground surface and is metal; as shown in FIG. 4(*b*), expect for the lower surface 7, the probe surface 5 also comprises a surrounding surface 9, and the lower surface 7 and the surrounding surface 9 are both metal. The lower surface 7 makes a direct contact with a medium below the probe 1 such as grass, and the sensitivity of the capacitance sensor 150 can be effectively improved by improving the conductivity of the lower surface 7. The surrounding surface 9 also plays an important role of improving the sensitivity of the capacitance sensor 150. In one aspect, the surrounding surface 9 also makes a contact with the medium below the probe, and particularly, when the grass is higher, a contact area between the medium and the surrounding surface 9 is larger. In the other aspect, more charges are accumulated on the edge of the polar plate of the capacitance C1, due to the arrangement of the surrounding surface 9, the charges accumulated on the edge of the polar plate of the capacitance C1 can be effectively used, and therefore, the sensitivity of the capacitance sensor 150 can be improved.

In the present embodiment, an interval between the polar plate 3 and the outer layer 19 of the cladding layer is controlled to be smaller than or equal to a preset distance, such that the metal polar plate is close to the metal outer layer as much as possible, and the sensitivity of the capacitance sensor 150 can be further increased.

Figure 6:
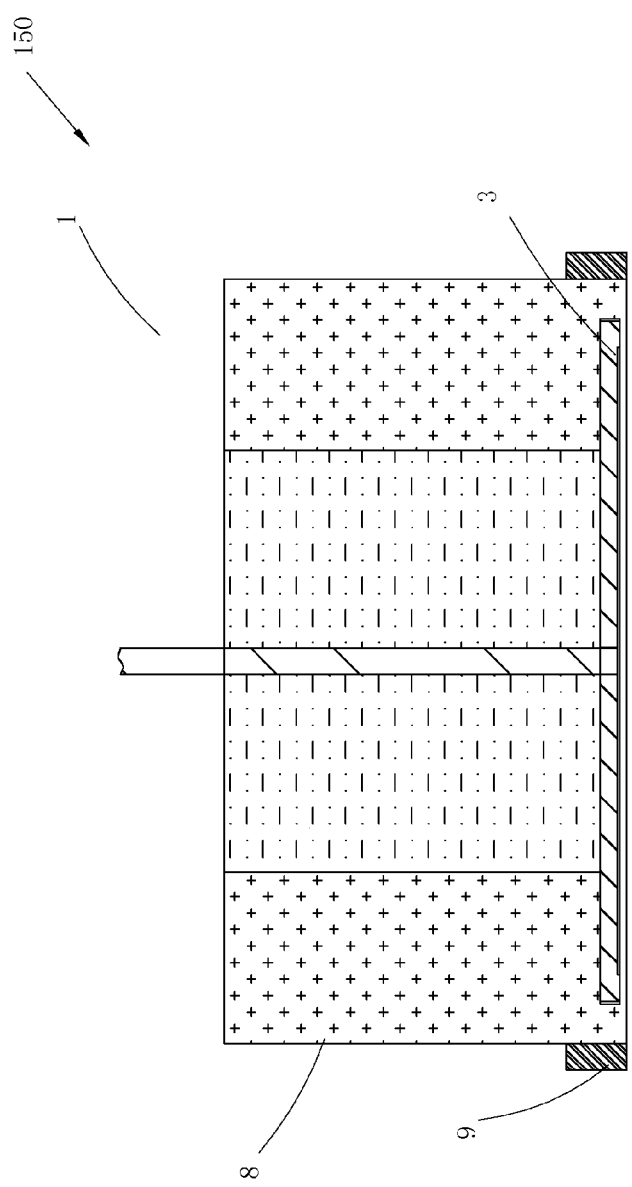
FIG. 6 is a structural schematic diagram of a capacitance sensor of a third embodiment of the present invention.

FIG. 6 is a structural diagram of the probe 1 of a third embodiment of the present invention. The probe 1 comprises a polar plate 3, which is a metal polar plate, and the polar plate 3 is disposed in a sensor shell 8 which is made of an insulating material. The probe 1 comprises a cladding layer, cladding the polar plate 3 around the longitudinal axis, the conductivity of the outer surface of the cladding layer is larger than or equal to $10^{-9}$ s/m, and specifically, the cladding layer is metal. In the present embodiment, the probing surface 5 comprises a surrounding surface 9, i.e., the outer surface of the cladding layer. In the present embodiment, the metal polar plate faces to the ground surface, therefore, although the lower surface of the probe 1 is the insulating material, when a potential difference exists between the metal polar plate and the ground surface, the lower surface of the probe 1 can still sense charges, therefore, the lower surface of the probe 1 can also be the probing surface 7. That is to say, in the present embodiment, the probing surface 5 comprises a first part of which the conductivity is smaller than or equal to $10^{-9}$ s/m, i.e., the lower surface 7 of the probing surface 5, and a second part of which the conductivity is larger than or equal to $10^{-9}$ s/m, i.e., the surrounding surface 9 of the probing surface 5. It is understandable that in other embodiments, the metal polar plate may not face to the ground surface, and for example, is vertical to the ground surface, and then the probing surface is the surrounding surface or other surface of the probe sensing the charges under the action of the metal polar plate.

The sensitivity of the capacitance sensor 150 is also related to a distance between the probe 1 and the ground surface, specifically, related to the distance between the end of the probe 1 and the ground surface. The smaller the distance between the probe 1 and the ground surface is, the higher the sensitivity of the capacitance sensor 150 is. In the first embodiment, the sensitivity of the capacitance sensor 150 is related to a distance between the lower surface 7 of the probing surface 5 and the ground surface, that is, related to the distance between the lower surface 7 of the probing surface 5 and a bottom surface of the wheel set. The smaller the distance between the lower surface 7 of the probing surface 5 and the ground surface is, the higher the sensitivity of the capacitance sensor 150 is. Therefore, in order to improve the sensitivity of the capacitance sensor 150, the lower surface 7 of the probing surface 5 should approach to the ground surface as much as possible, that is, approach to the bottom surface of the wheel set as much as possible. However, when the distance between the lower surface 7 of the probing surface 5 and the ground is oversmall, in a moving process of the automatic mower 100, the probing surface 5 possibly makes a contact with the ground surface, especially when the automatic mower 100 moves on an uneven ground surface. If the probing surface 5 makes a contact with the ground surface, then no potential difference exists between the two poles of the capacitance C1, and the electric signal output by the capacitance sensor 150 cannot correctly reflect whether the ground is the grassland, as a result, the automatic mower 100 cannot work safely. In other aspect, the probe 1 makes a direct contact with the ground surface, the probe 1 may be damaged, especially, in a moving process of the automatic mower 100, when the probe 1 and the ground surface collide, the probe 1 is impacted and damaged.

In order to avoid the contact between the probe 1 and the ground surface and increase the sensitivity of the capacitance sensor 150 as much as possible, in the first embodiment, the lower surface 7 of the probing surface 5 is controlled to be higher than the bottom surface of the wheel set, and a distance between the lower surface 7 and the bottom surface of the wheel set is larger than or equal to 10 mm and smaller than or equal to 50 mm. Of course, in order to more reliably avoid the contact between the probe 1 and the ground surface, the distance between the lower surface 7 of the probing surface 5 and the bottom surface of the wheel set can be controlled to be larger than or equal to 15 or 20 mm, etc. In order to further increase sensitivity of the capacitance sensor 150, the distance between the lower surface 7 of the probing surface 5 and the bottom surface of the wheel set can be controlled to be smaller than or equal to 40 or 30 mm, etc. In the present embodiment, the distance between the probe 1 and the ground surface is controlled to be smaller than the distance between the end of the cutting module 120 (i.e., end of the blade) and the ground surface. That is to say, in a height direction, the end of the probe 1 is lower than a cutting plane.

In the present embodiment, in order to prevent the ground surface from making a contact with and damaging the probe 1 and increase the sensitivity of the capacitance sensor 150 as much as possible, a distance between the probe 1 and the bottom surface of the wheel set is controlled to be adjustable. Specifically, as shown in FIG. 2, the capacitance sensor comprises a connecting part 14 connected to the probe 1 and the shell 110, and the connecting part 14 can drive the probe 1 to move relative to the shell 110. Specifically, the connecting part 14 can drive the probe 1 to move in a height direction relative to the shell 110. In the present embodiment, the connecting part 14 is made of a soft material, specifically, made of rubber. When the probe 1 is subjected to an action force along the height direction, for example, when the probe 1 makes a contact with the ground surface, the connecting part 14 is shrunk upwards to drive the probe 1 to move upwards, such that the probe 1 gets away from the ground surface; when the probe 1 is not subjected to the action force of the ground surface any more, the connecting part 14 extends downwards under an action of elasticity per se to drive the probe 1 to move downwards, such a smaller interval is restored between the probe 1 and the ground surface. Thus, the smaller interval is always kept between the probe 1 and the ground surface, therefore, it is ensured that the capacitance sensor 150 has high sensitivity, and the ground surface is prevented from colliding and damaging the probe 1.

In the present embodiment, the connecting part 14 can also drive the probe 1 to swing in a horizontal direction relative to the shell 110. When the automatic mower 100 moves on an uneven ground surface, the probe 1 makes a contact with the ground surface, and at this point, except for the force along the height direction, the probe 1 is also subjected to a force along a horizontal direction. Since the connecting part 14 has flexibility, when the probe 1 is also subjected to the force along the horizontal direction, one end of the connecting part 14 connected to the probe 1 is deviated in the horizontal direction relative to one end connected to the shell 110, that is, the connecting part 14 drives the probe 1 to swing along the horizontal direction relative to the shell 110. When the probe 1 is not subjected to a contact force of the ground surface any more, the connecting part 14 is restored to an original shape under the elasticity per se to drive the probe 1 to restore to the original location relative to the shell 110. Therefore, when the probe 1 makes a contact with the ground surface, the probe 1 is in a state of swinging in the horizontal direction relative to the shell 110. The connecting part 14 drives the probe 1 to swing in the horizontal direction relative to the shell 110, and can avoid a friction between the probe 1 and the ground surface when the probe 1 makes a contact with the ground surface and damage to the probe 1.

As shown in FIG. 2, in the present embodiment, the connecting part 14 comprises a through hole along the longitudinal axis X for a lead 13 electrically connected to the probe 1 and the control module to penetrate through. Since the connecting part 14 has flexibility, when the probe makes a contact with the ground surface, the connecting part 14 can absorb vibration caused by collision to protect the circuit.

In the present embodiment, by controlling the distance between the probe 1 and the ground surface, when the automatic mower 100 moves on the grass, the probe 1 is kept in contact with the grass, that is, the probing surface 5 makes a contact with the grass. That is to say, a distance between the probe 1 and the ground surface is smaller than a height of a medium (grass) on the working plane (lawn). Through test, when the probing surface 5 makes a contact with the grass, the electric signal output by the capacitance sensor 150 is changed more obviously compared with the electric signal output by the capacitance sensor 150 when the non-grassland is below the probe 1. That is to say, when the automatic mower 100 moves on the grass, when the probing surface 5 makes a contact with the grass, the charging and discharging rates of the capacitance sensor 150 is slower compared with that when the probing surface 5 does not make a contact with the grass. Therefore, the probe 1 contacting with the grass makes the detection of the capacitance sensor 150 of the grassland more sensitive.

In other embodiments, the capacitance sensor 150 can use other height adjusting structures to adjust a height of the probe 1 relative to the shell 110 and a specific solution is described below.

The sensitivity of the capacitance sensor 150 is also related to a surface area of the probe, specifically, related to the area of the probing surface 5. The larger the area of the probing surface 5 is, the higher the sensitivity of the capacitance sensor 150 is. In the first embodiment of the present invention, the probing surface 5 comprises a lower surface 7 and a surrounding surface 9, and the area of the probing surface 5 is larger than or equal to 28 cm$^2$. In the first embodiment of the present invention, the area of the probing surface 5, i.e., the area of the metal polar plate is larger than or equal to 28 cm$^2$. In the second embodiment of the present invention, the area of the metal polar plate is controlled to be larger than or equal to 28 cm$^2$. Of course, in order to further improve the sensitivity of the capacitance sensor 150, the area of the probing surface 5 or polar plate can be set to be larger than or equal to 35 cm$^2$, or 40 cm$^2$ or 45 cm$^2$, etc.

Figure 7:
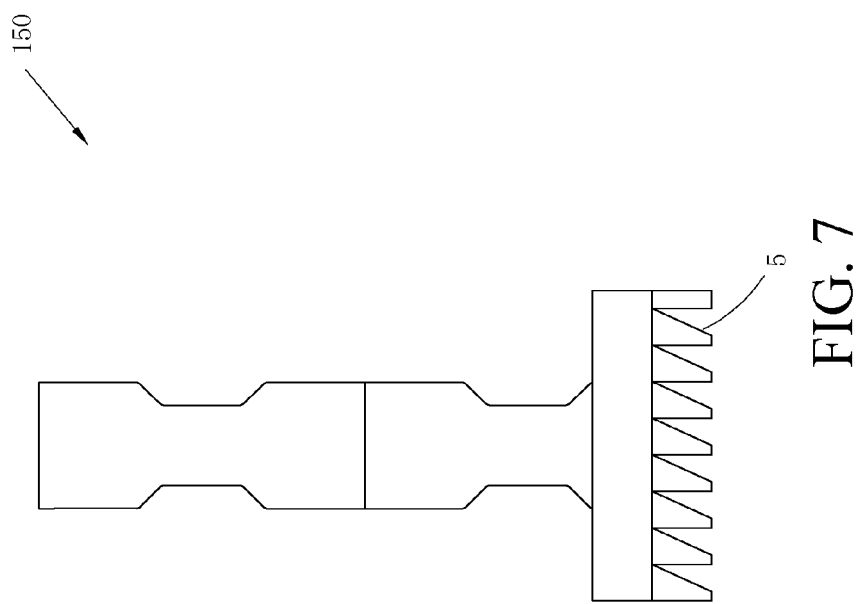
FIG. 7 is a structural schematic diagram of a capacitance sensor of a fourth embodiment of the present invention.

As shown in FIG. 7, in a fourth embodiment of the present invention, in order to increase the area of the probing surface 5 as much as possible, the probe 1 comprises a concavo-convex surface, and the probing surface 5 comprises the concavo-convex surface. Specifically, the lower surface of the probing surface is wavy, hence, on the basis of not increasing the diameter of the probe 1, the area of the probing surface 5 can be further increased, and the aim of improving the sensitivity is achieved.

Figure 8:
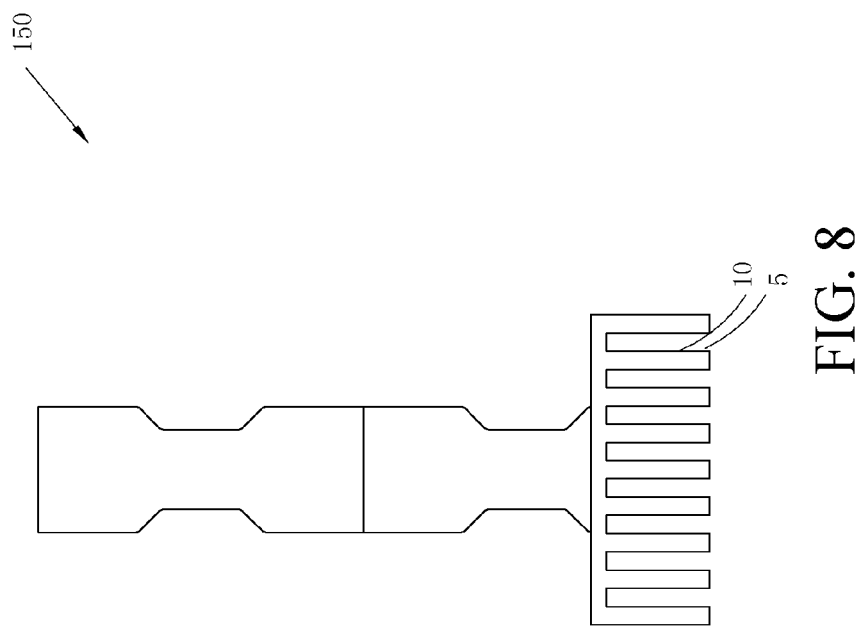
FIG. 8 is a structural schematic diagram of a capacitance sensor of a fifth embodiment of the present invention.

As shown in FIG. 8, in a fifth embodiment of the present invention, the probe 1 comprises a plurality of teeth, extending downwards along a height direction, the probing surface 5 comprises surface of the teeth. Specifically, in the present embodiment, the probing surface 5 comprises a side surface 10, vertical to the working surface of the automatic mower 100, and the conductivity of the side surface 10 is larger than or equal to $10^{-9}$ s/m. In the present embodiment, the probing surface 5 extends along a height direction, the surface of the teeth can serve as the probing surface 5, the probe 1 can comprise a plurality of teeth, hence, the area of the probing surface 5 is greatly increased. In the present embodiment, the probe 1 is comb-shaped, gaps for the grass to leak through are formed among adjacent teeth, such that the probing surface 5 can make a full contact with the grass without affecting the task operation of the cutting module 120. In the present embodiment, preferably, the gaps among the adjacent teeth face to a moving direction of the automatic mower 100, that is, the side surface 10 of the probing surface 5 is parallel with the moving direction of the automatic mower 100, such that when the automatic mower 100 moves, the grass can better leak through the gaps among the teeth. Of course, in other embodiments, the teeth may not be vertical to the working surface of the automatic mower 100 and is inclined for a preset angle relative to the working surface of the automatic mower 100, that is, the side surface 10 of the probing surface 5 is inclined for a preset angle relative to the working surface of the automatic mower 100.

In the embodiment above, it can be understandable that the bottom of the shell 110 is defined relative to the top and side part of the shell 110, and refers to the part of the shell 110 facing to the ground surface without a height limitation.

In some embodiments, the lower surface 7 of the probing surface 5 can be an arc surface, for example, a spherical probe.

In some embodiments, the capacitance sensor 150 can also detect a cut grassland and an uncut grassland. For example, according to the medium below the probe 1, proportions of air and grass of which are different, or according to a fact whether the grass makes a contact with the probing surface 5, in that case, the probe 1 can be slightly higher than the cutting blade.

In some embodiments, at least one of the capacitance sensor is disposed on the front end or back end of the shell.

In some embodiments, the moving module comprises a front wheel and a back wheel, and at least one of the capacitance sensors is disposed at the front side of the front wheel or the back side of the back wheel.

In some embodiments, the moving module comprises a front wheel and a back wheel, and at least one of the capacitance sensors is disposed between the front side of the front wheel and the back side of the back wheel.

In some embodiments, at least two groups of capacitance sensors are comprised and are respectively disposed on both sides of the shell.

In the second embodiment of the present invention, reference is made to FIG. 4(*a*), which is a sectional view of the capacitance sensor 150. As shown in FIG. 4(*a*), a capacitance sensor 150 comprises a polar plate 3 and an end cover (i.e., the outer layer 19 of the cladding layer) and an insulating interlayer (i.e., the inner layer 17 of the cladding layer). The end cover is disposed outside the polar plate 3 and configured to protect the polar plate 3, and avoids a damage such as collision or friction to the polar plate 3. The end cover is made of a conductive material, and the insulating interlayer is disposed between the polar plate 3 and the end cover.

When the capacitance sensor 150 works, the end cover 3 transmits an electric field to an article to be detected to detect the article to be detected. Since the end cover is a conductor and has high conductivity, the end cover is favorable for the transmission of the electric field of the polar plate 3, and a sensitivity of the capacitance sensor 150 is enhanced effectively, such that a detection effect of the capacitance sensor 150 is better.

In the present embodiment, vegetation is taken as an example of the article to be detected.

The polar plate 3 is configured to detect the vegetation as one electrode of the capacitance sensor 150, the ground serves as the other electrode of the capacitance sensor 150, thus, the polar plate 3 and the ground constitute a capacitance sensor, and simplicity and cost reduction are realized.

In the present embodiment, the polar plate 3 is a metal thin plate, such that a detection range of the polar plate 3 is larger. The end cover is disposed outside the polar plate 3, that is, the end cover is disposed at one side of the polar plate 3 facing to the vegetation. The end cover can be made of a conductive material such as metal, conductive alloy or superconducting material. In the present embodiment, the end cover is a metal end cover and has very small resistivity and very large conductivity, that is, the conductive performance of the metal is better, and therefore, the metal end cover is favorable for the transmission of the electric field of the polar plate 3 toward a vegetation direction.

The insulating interlayer enables the polar plate 3 and the end cover to be insulated. Under a general condition, the end cover is exposed in an outside environment, and since the end cover is made of the conductive material and very easily conducts static electricity in the outside environment, the insulating interlayer is configured to protect the polar plate 3 from being affected by outside static electricity. Specifically, the insulating interlayer is an insulating thin layer, for example, a thickness of the insulating interlayer is in a micrometer order, such that when the insulating interlayer protects the polar plate 3 from being affected by the outside static electricity, electric field transmission between the polar plate 3 and the vegetation is not affected. Further, the insulating interlayer is made of insulating plastic or rubber, such that an electric insulating effect between the polar plate 3 and the outside environment is better. In other embodiments, the material of the insulating interlayer is not limited thereto, and can be other insulating materials.

The capacitance sensor 150 can also comprise a base plate 21, disposed on the other side of the polar plate 3, and the polar plate 3 is embedded on the base plate 21 which is configured to fix the polar plate 3. Thus, the polar plate 3 is disposed more steadily.

The capacitance sensor 150 in the present embodiment comprises the base plate 21, the polar plate 3, the insulating interlayer and the end cover in sequence when viewed in a direction from the base plate 21 to the end cover, wherein the base plate 21, the polar plate 3 and the insulating interlayer are in parallel and are laminated together, such that the structure is compact.

The capacitance sensor 150 can also comprise a lead 13 and a fixing structure 23, the lead 13 penetrates through the base plate 21 to be connected to the polar plate 3, that is to say, the base plate 21 is provided with a through hole adaptive to the lead 13, one end of the lead 13 penetrates through the through hole to be connected to the polar plate 3, and the other end is lead out to a direction away from the end cover to connect the circuit of the capacitance sensor 150. The fixing structure 23 surrounds the lead 13 and abuts against the base plate 21, and the fixing structure 23 is configured to fix the lead 13. Thus, the location of a part of the lead 13 close to the polar plate 3 can be limited. Preferably, the fixing structure 23 is made of sponge, and since the sponge has elasticity, the lead 13 can move relative to the fixing structure 23, and the lead 13 is not easily broken off when the capacitance sensor 150 is collided accidentally.

The capacitance sensor 150 can further comprise a cylindrical sensor shell 25, the side wall of the sensor shell 25 defines an inner cavity, the fixing structure 23 and the base plate 21 are disposed in the inner cavity, the base plate 21 is vertical to a central axis of the sensor shell 25, the fixing structure 23 and the base plate 21 abut against the side wall of the sensor shell, the side wall of the sensor shell 25 and the end cover are connected together in a matching manner, and the sensor shell 25, the fixing structure 23 and the end cover are matched together to protect the metal polar plate 3. Thus, the sensor shell 25, the fixing structure and the end cover can seal the polar plate 3 in the capacitance sensor 150 to prevent the polar plate 3 from being collided in respective directions and protect the polar plate 3. Specifically, in the present embodiment, the inner cavity in the sensor shell 25 is filled with the fixing structure 23 of the sponge and the base plate 21 together, the end cover is matched and connected to the side wall of the capacitance sensor 25 together from the bottom of the sensor shell 25, and the end cover and the side wall of the sensor shell 25, the end cover and the insulating interlayer and the insulating interlayer and the polar plate 3 are tightly matched, such that the polar plate 3 is set more firmly.

Reference is made to FIG. 4(*b*), the end cover is a round cover and comprises a flange 27, the flange 27 is disposed on one side of the end cover facing to the sensor shell 25, the flange 27 surrounds the side wall of the sensor shell 25, and the flange 27 and the side wall of the sensor shell 25 are connected together through threads. Thus, the end cover and the side wall of the sensor shell 25 are twisted together through the threads to realize connection, and are simple to mount. The end cover and the side wall of the sensor shell 25 are detachably connected, and the polar plate 3 is convenient to maintain. Further, since the end cover is made of the metal material, wear resistance is better, therefore, the metal flange 27 can protect the sensor shell 25 from the side surface of the sensor shell 25. The metal flange 27 is disposed on the side surface of the sensor shell 25, it is favorable for the polar plate 3 to transmit an outward radiated electric field from the side wall of the sensor shell 25 to the outside, the vegetation on the side surface of the sensor shell 25 can be recognized, and the sensitivity of the capacitance sensor 150 can be further improved.

Reference is made to FIG. 4(*a*), and the capacitance sensor 150 comprises a polar plate 3, an end cover and an insulating interlayer. The end cover is planar. The capacitance sensor 150 also comprises a sensor shell 25, and the side wall of the sensor shell 25 and the end cover are connected by screws. Thus, the connection between the side wall of the sensor shell 25 and the end cover is simple, and the end cover is planar and is simple in a manufacture process and cost-saving.

Reference is made to FIG. 4(*c*), which is a detection principle diagram of a capacitance sensor of the second embodiment. An input end of the signal processing circuit 160 is connected to the polar plate 3; and an input end of a processor 170 is connected to an output end of the signal processing circuit 160.

In a working state of the capacitance sensor 150, the polar plate 3 will transmit an electric field to the vegetation to detect the vegetation. The end cover is located between the polar plate 3 and the vegetation, the end cover is made of a conductive material and has high conductivity, the end cover is favorable for electric field transmission of the polar plate 3, and sensitivity of the capacitance sensor 150 is effectively enhanced, such that the vegetation detection effect of the capacitance sensor 150 is better. The polar plate 3 transmits a vegetation detection signal to the processor 170 via the signal processing circuit 160, and the automatic mower 100 can execute a work task according to a vegetation detecting condition of the polar plate 3, such that a vegetation cutting effect is better.

The polar plate 3 serves as an electrode of the capacitance sensor 150, the ground serves the other electrode of the capacitance sensor 150, and a condition of the grassland can be judged by detecting a change of the capacitance between the polar plate 3 and the ground. The signal processing circuit 160 outputs square waves according to a signal transmitted by the capacitance sensor 150. When the polar plate 3 detects the vegetation, a dielectric constant between the polar plate 3 and the ground surface is increased, the capacitance between the polar plate 3 and the ground is increased, and the frequency of the square waves output by the signal processing circuit 160 is reduced. When there is no vegetation, the dielectric constant between the polar plate 3 and the ground is reduced, the capacitance between the polar plate 3 and the ground surface is also reduced, and the frequency of the square waves output by the signal processing circuit 160 is increased. Therefore that the processor 170 can judge a vegetation condition according to the square wave frequency output by the signal processing circuit 160, and a working state of the automatic mower 100 is controlled.

It should be noted that the output signal of the signal processing circuit 160 is not limited thereto, and can be in other signal forms, for example, can be a level change as long as the condition that the capacitance sensor 150 detects the grassland is indicated.

Specifically, the signal processing circuit 160 comprises a schmitt trigger ST, an input end of the schmitt trigger ST is connected to the polar plate 3, and an output end of the schmitt trigger ST is connected to an input end of the processor 170. When the polar plate 3 detects the vegetation, an output signal of the schmitt trigger ST is changed to realize that the automatic mower 100 automatically recognizes the vegetation. Further, the signal processing circuit 160 also comprises a base capacitance and a resistor R. One end of the basic capacitance is connected to the input end of the schmitt trigger ST, and the other end is grounded. Both ends of the resistor R are connected between the input end and output end of the schmitt trigger ST in parallel. If there is vegetation below the polar plate 3 or the polar plate 3 makes a contact with the vegetation, the basic capacitance is changed to cause the change of the output signal of the schmitt trigger ST to realize vegetation detection, and the vegetation is convenient and effective to cut. In addition, the signal processing circuit 160 also comprises a power source Vcc and a filter capacitor. The power source Vcc is connected to a power source end of the schmitt trigger ST and is configured to provide working electricity for the schmitt trigger ST. The filter capacitor is connected between the power source end of the schmitt trigger ST and the ground, has a voltage stabilizing action, and is configured to stably connect the power voltage of the schmitt trigger ST, such that the schmitt trigger ST works stably.

One or more capacitance sensors 150 are disposed, one or more signal processing circuits 160 are disposed, a quantity of the signal processing circuit 160 is same as that of the capacitance sensor 150, and each capacitance sensor 150 is correspondingly connected to one signal processing circuit 160. Thus, an interference among a plurality of signal processing circuits 160 can be prevented, such that the processor 170 can accurately judge a condition that the capacitance sensor 150 detects the vegetation, such that the automatic mower 100 can accurately execute a cutting task. In the present embodiment, two capacitance sensors 150 are disposed to detect the vegetation accurately.

Other height adjusting embodiments of the probe: a capacitance sensor of a traditional automatic mower is fixed on the shell, the height cannot be adjusted, since a recognition accurate rate on the grassland will be increased due to a contact between the capacitance sensor and the grass, while when the grassland is shorter and the capacitance sensor is higher, the automatic mower easily generates a misjudgment and does not mow the grass. In addition, since the capacitance sensor is higher, the automatic mower cannot recognize the grassland in a current short grass area, that is, the automatic mower judges that there is no grassland in the local, at this point, even if a high grass area exists between the short grass area, the automatic mower will not pass by the current short grass area to walk to the high grass area, i.e., a "short grass siege" phenomenon occurs. Therefore, the lawn that should be trimmed is not trimmed, and working efficiency of the traditional mower is lower.

Therefore, it is necessary to design a novel automatic mower specific to the problem that a traditional capacitance sensor is fixed on the shell and a height cannot be adjusted, a height of its capacitance sensor relative to the ground can be adjusted, the height of the capacitance sensor can be adjusted according to the height of the grass needing to be cut, and the misjudgment that the machine does not cut the grassland is reduced, such that a lawn trimming effect is ideal and working efficiency is improved.

Sixth Embodiment

Figure 9:
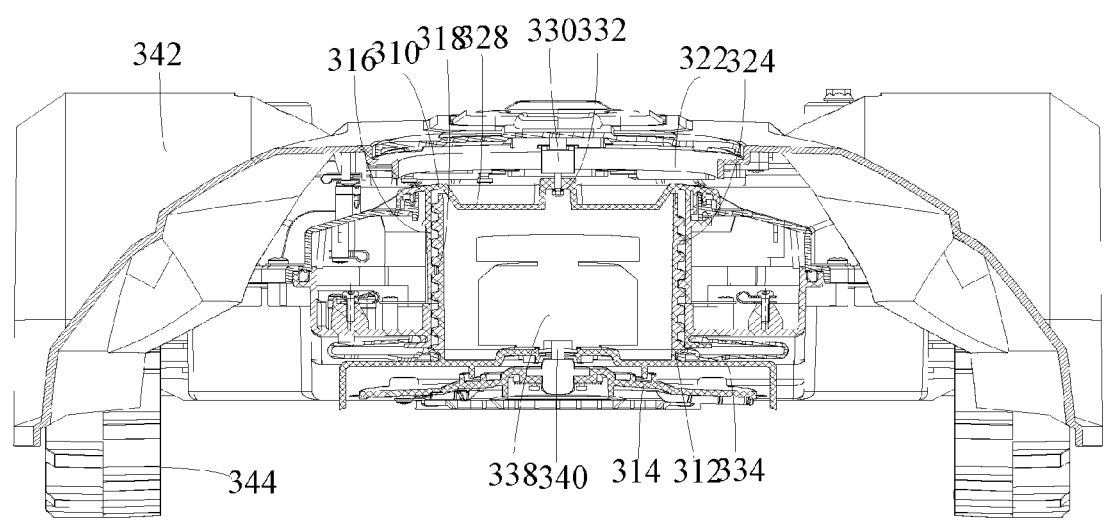
FIG. 9 is a sectional view of a mower of a sixth embodiment.
Figure 10:
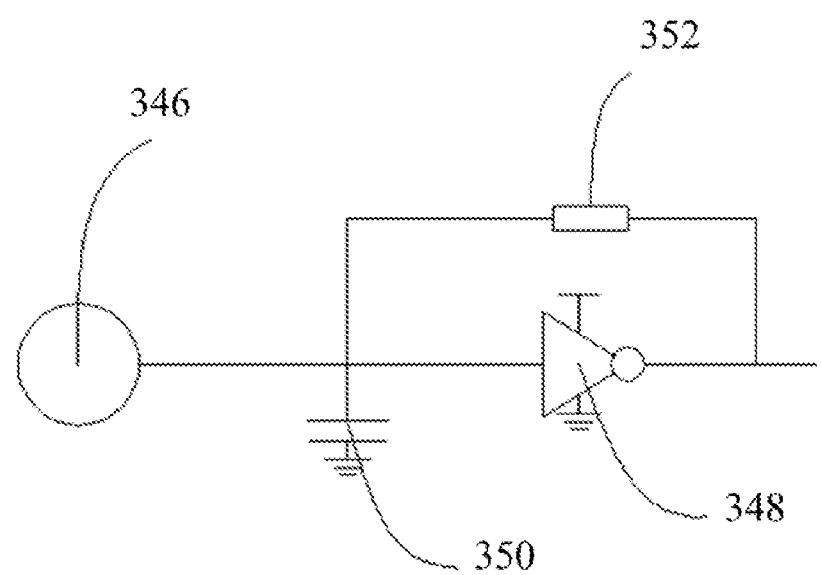
FIG. 10 is a schematic diagram of a signal processing circuit of the mower of the embodiment as shown in FIG. 9.
Figure 11:
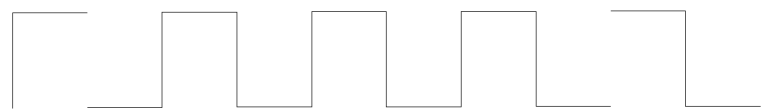
FIG. 11 is a schematic diagram of an output signal of the signal processing circuit of the embodiment as shown in FIG. 9.

Reference is made to FIGS. 9-11, FIG. 9 is a sectional view of an automatic mower of the present embodiment, FIG. 10 is a schematic diagram of a signal processing circuit of an automatic mower of the present embodiment, and FIG. 11 is a schematic diagram of an output signal of the signal processing circuit of the present invention. A normal advancing direction of the automatic mower is defined as the front of the automatic mower, and one direction opposite to the front is the back.

As shown in FIG. 9, an automatic mower is configured to cut vegetation located on a working surface. The automatic mower comprises a shell and a sensing component 132, disposed on the shell. The sensing component 132 comprises a capacitance sensor (short for sensor hereinafter) and a height of the sensor relative to the working surface is adjustable and is configured to sense the vegetation.

The automatic mower further comprises a cutting cutterhead 314, disposed on the shell, a height of the cutting cutterhead 314 relative to the working surface can be adjusted, and the cutting cutterhead 314 is configured to cut the vegetation.

In the present embodiment, the working surface is the ground and is not limited thereto in other embodiments, and the working surface can be a surface of a building, etc.

In the present embodiment, the heights of both the sensing component 312 and the cutting cutterhead 314 can be adjusted relative to the working surface. It is noted that in other embodiments, the height of the cutting cutterhead 314 relative to the working surface can be adjusted independently.

In the present embodiment, the mower also comprises a rotary component 310 which can rotate and has a first side wall 316 vertical to the working surface, and rotary teeth 318 are disposed on the surface of the first side wall 316; the sensing component 312 has a second side wall 322 vertical to the working surface, the second side wall 322 is provided with rotary threads 324 relative to the surface of the first side wall 316, the rotary threads 324 and the rotary teeth 318 are meshed, the sensor is disposed on the second side wall 322, and the sensing component 312 moves relative to the working surface along with rotation of the rotary component 310.

In the present embodiment, the rotary component 310 comprises a transverse connecting rod 328, parallel with the working surface, and the transverse connecting rod 328 is connected to the first side wall 316.

The rotary component 310 can rotate and can subsequently drive the sensing component 312 to move up and down. The rotary component 310 is driven to rotate in a manual, automatic or manual and automatic combined manner. The mower in the present embodiment can automatically drive the rotary component 310 to rotate by a height adjusting motor 330, the height adjusting motor 330 has a first output shaft 332, the rotary component 310 is disposed on the first output shaft 332, and the height adjusting motor 330 can drive the rotary component 310 to rotate through a first output shafts 332. Specifically, the height adjusting motor 330 is located above the rotary component 310, the first output shaft 332 is matched and connected to the center of a transverse connecting rod 328, therefore, under the driving of the height adjusting motor 330, the rotation of the first output shaft 332 can drive the rotary component 310 to rotate. In the present embodiment, the height adjusting motor 330 is a stepmotor, which can convert an electric pulse signal into angular displacement, and when the stepmotor receives one pulse signal, the stepmotor rotates for a corresponding angle according to a set direction, such that the rotary component 310 is driven to rotate for a corresponding angle.

The sensing component 312 has a second side wall 322 vertical to the working surface, the sensor is disposed on the second side wall 322 and the probe of the sensor faces to the working surface and is configured to sense the vegetation.

The second side wall 322 is opposite to the first side wall 316 and the second side wall 322 and the first side wall 316 are both vertical to the working surface. In order to enable the height of the sensor fixedly connected to the second side wall 322 to be adjusted up and down, rotary threads 324 are disposed on the surface of one side of the second side wall 322 opposite to the rotary teeth 318, and the rotary threads 324 are meshed with the rotary teeth 318, such that the rotary component 310 and the sensing component 312 can perform relative circumferential movement and up-down movement. In the present embodiment, since the rotary component 310 is kept unchanged in the height direction, when the rotary component 310 is driven to rotate, the rotary component 310 performs circumferential movement, and the sensing component 312 performs up-down movement to be favorable for the probe of the sensor to sense the vegetation.

In other embodiments, the sensor is telescopic per se. For example, the sensor is manufactured by adopting an elastic material, and the height of the sensor relative to the working surface can be adjusted along with a height of the vegetation. When the vegetation is shorter, the sensor is in a tensile state due to the gravity per se, and can approach to the vegetation. When the vegetation is higher, the vegetation gives an upward force to the sensor to compress the sensor, and the sensor is higher relative to the working surface. Thus the height of the sensor relative to the working surface can be freely adjusted according to the height of the vegetation, and the automatic mower can effectively recognize and cut the vegetation.

It should be noted that in the present embodiment, the circumferential movement of the rotary teeth 318 relative to the rotary threads 324 is adopted to drive the sensing component 312 to move up and down. In other embodiments, the sensing component 312 can move up and down relative to the working surface by adopting other manners, for example, other mechanical structures or automatic control structures, etc., can be adopted.

Further, about the locations of the rotary teeth 318 and the rotary threads 324, the rotary teeth 318 can be located on the surface of one side of the first side wall 316 away from a rotary shaft of the rotary component 310, and can also be located on the surface of one side of the first side wall 316 close to a rotary shaft of the rotary component 310. The rotary threads 324 can be located on the surface of one side of the second side wall 322 away from a rotary shaft of the rotary component 310, and can also be located on the surface at one side of the second side wall 322 close to a rotary shaft of the rotary component 310 as long as the two can be meshed. In the present embodiment, the second side wall 322 is located at one side of the first side wall 316 close to the rotary shaft of the rotary component 310, and is opposite to the first side wall 316, the rotary threads 324 are disposed on the surface of the second side wall 322, that is, the rotary threads 324 are located on the surface of one side of the second side wall 322 away from the rotary shaft of the rotary component 310, the rotary threads 324 and the rotary teeth 318 can be meshed, the rotary teeth 318 can rotate circumferentially along the rotary threads 324, while a height of the rotary teeth 318 is unchanged so as to drive the sensing component 312 to move up and down.

It should be noted that in other embodiments, the second side wall 322 can also be located at one side of the first side wall 316 away from the rotary shaft of the rotary component 310, its rotary threads 324 are located at the surface of one side of the second side wall 322 close to the rotary shaft of the rotary component 310, while the rotary teeth 318 are located at the surface of one side of the first side wall 316 away from the rotary shaft of the rotary component 310 and meshed with the rotary threads 324, therefore, rotation of the rotary component 310 along with the rotary threads 324 can be realized, and the sensing component 312 is driven to move up and down.

In the present embodiment, the sensing component 312 also comprises a sensor connecting rod 334 connected to the second side wall 322 and located below the second side wall 322; the sensor is disposed on the sensor connecting rod 334, faces to the working surface and is configured to sense the vegetation, connection between the sensor and the sensor connecting rod 334 can be fixed connection or detachable connection, in the present embodiment, the fixed connection is adopted, and the sensor correspondingly moves up and down along with up-down movement of the sensing component 312.

The automatic mower in the present embodiment also comprises a cutting motor 338, located at one side of the cutting cutterhead 314 away from the working surface, and the cutting motor 338 provides power for the cutting cutterhead 314.

The automatic mower in the present embodiment further comprises a motor box (not shown), the motor box sleeves outside the cutting motor 338 and is located at one side of the cutting cutterhead 314 away from the working surface, and the second side wall 322 is a side wall of the motor box. The motor box gives an enough working space for the cutting motor 338, such that the cutting motor 338 does not interfere with other components when in work, in addition, the side wall of the motor box serves as the second side wall of the sensing component, the two are integrated, a weight of the cutting motor is reduced and a space occupied by components of the mower is reduced.

In the present embodiment, the cutting motor 338 is located on the bottom in the motor box, and a shell of the cutting motor 338, the bottom of the motor box and the sensor connecting rod 334 are fixedly connected by screws, and the three move up and down together.

The automatic mower also comprises a location sensor (not shown), located at the surface of one side of the second side wall 322 away from the rotary shaft of the rotary component 310. The location sensor is configured to sense a height from the motor box to the working surface. Thus, when the motor box, the cutting motor 38 and the sensor connecting rod 334 are descended to a minimal height or ascended to a maximal height, the location sensor can timely feed height information back to the automatic mower, such that the height adjusting motor 330 timely stops working and avoids energy waste, and the height adjusting motor 330 and the rotary component 310 are prevented from damage.

In the present embodiment, the cutting motor 338 has a rotatable output shaft 340, the cutting cutterhead 314 is fixedly connected on the output shaft 340 and rotates along with rotation of the output shaft 340, and the cutting motor 338 drives the cutting cutterhead 314 to execute a vegetation cutting operation by the output shaft 340.

In the present embodiment, the rotary component 310 and the cutting cutterhead 314 rotate around the same axis. Further, the first output shaft 332, a central axis of the motor box, a central axis of the cutting motor 338 and a rotary axis of the cutting cutterhead 314 are coincided, thus a gravity center is stable and mowing is uniform when the automatic mower mows the grass.

The automatic mower in the present embodiment also comprises a shell 342, configured to dispose the components of the automatic mower above, and an enough space is provided for the components such as the height adjusting motor 330, the rotary component 310, the sensing component 312, the cutting motor 338 and the cutting cutterhead 314 in the shell 342.

The automatic mower also comprises a walking component (not shown), the walking component comprises at least one wheel, and the sensor is located in front of or behind a walking direction of the walking component. The walking component in the present embodiment comprises a front wheel (not shown) and two back wheels 344, wherein the front wheel is a support wheel, the two back wheels 344 are disposed in parallel, are driving wheels and are located behind the automatic mower, and the automatic mower is driven by the driving wheels to walk. The sensor is disposed in front of the front wheel, or the sensor is disposed behind one of the back wheels 344, and the sensor can also be disposed between the two back wheels 344 or in other locations. Of course, the quantity of the sensors can be more, and a plurality of sensors are uniformly distributed at the periphery of all the wheels. Thus, a vegetation detection range of the sensing component 312 can be increased, and the vegetation is effectively cut. Besides, when the automatic mower is driven to a nonworking area, the sensor sends a signal that no grass is detected, at this point, the automatic mower is automatically returned to the vegetation area to continuously detect and cut the vegetation. Further, a condition that the automatic mower is driven to places such as a step or cliff where the automatic mower is damaged if continuing to advance can be avoided.

The automatic mower in the present embodiment further comprises a control device (not shown), which is located on the shell 342, is electrically connected to the cutting motor 338, the sensor and the height adjusting motor 330, and is configured to control the automatic mower to work and control the components such as the height adjusting motor 330, the cutting motor 338 and the sensor to work.

Reference is made to FIG. 10, which is a schematic diagram of a signal processing circuit of an automatic mower of the present embodiment, and the signal processing circuit comprises a schmitt trigger 348, an input capacitor 350 and a resistor 352. An input end of the schmitt trigger 348 is connected to a probe 346 of the sensor, and an output end of the schmitt trigger 348 (i.e., the output end of the signal processing circuit) is connected to the control device.

The sensor is a capacitance sensor, including a detecting electrode, the detecting electrode is configured to sensor vegetation and a height of the detecting electrode relative to the working surface is adjustable. The sensor also comprises a reference electrode opposite to the detecting electrode. The detecting electrode approaches to the working surface, and when the vegetation approaches to the detecting electrode, the capacitance of the capacitance sensor is changed. Specifically, the probe 346 serves as the detecting electrode of the capacitance sensor, and the reference electrode is a circuit of the signal processing circuit or the ground. Under both conditions that the probe 346 senses the vegetation or not, a capacitance value of the capacitance sensor is different, and a reference value of an output signal of the signal processing circuit is also different.

Reference is made to FIG. 11, which is a schematic diagram of an output signal of a signal processing circuit of the present embodiment, and when the automatic mower walks on the vegetation, an output signal of the signal processing circuit will be different along with a fact whether the probe 346 senses the vegetation. Specifically, as shown in FIG. 11, the signal processing circuit outputs a square wave signal, and when the probe 346 does not sense the vegetation, the frequency of a square wave signal is larger and a period is smaller. When the probe 346 senses the vegetation, the frequency of the square wave signal is smaller and the period is larger. That is, according to the output signal of the signal processing circuit, the control device can judge whether the probe 346 recognizes the vegetation. If the probe 346 recognizes the vegetation, the control device can control the automatic mower to cut the vegetation or continuously walk. If the probe 346 does not recognize the vegetation, the control device controls the height adjusting motor 330 to correspondingly adjust a height of the sensing component 312 relative to the vegetation, so as to further adjust a height of the sensor relative to the vegetation, and the height of the probe 346 relative to the vegetation can also be adjusted so as to quickly and sensitively recognize the vegetation and improve working efficiency.

It should be noted that in other embodiments, the output signal of the signal processing circuit is noted limited thereto. When the probe 346 senses the vegetation, the output signal of the signal processing circuit can be other signals, for example, a level signal as long as it can indicate whether the probe 346 senses the vegetation.

According to the automatic mower, since the height of the sensor relative to the working surface can be automatically adjusted, a user can adjust the height of the sensor according to a vegetation height, when the vegetation is shorter, the height of the sensor is reduced, and the automatic mower can recognize the vegetation without generating a misjudgment, such that the cutting cutterhead is started to cut the vegetation without leaking the vegetation that should be trimmed, a cutting effect is better and cutting efficiency is higher.

Seventh Embodiment

Different from the first embodiment, in the present embodiment, the height of the whole sensing component relative to the working surface may not be adjusted, only the height of the sensor relative to the working surface can be adjusted, in addition, the sensing component and the adjustment of single sensors can be adjusted to facilitate vegetation cutting.

Figure 12:
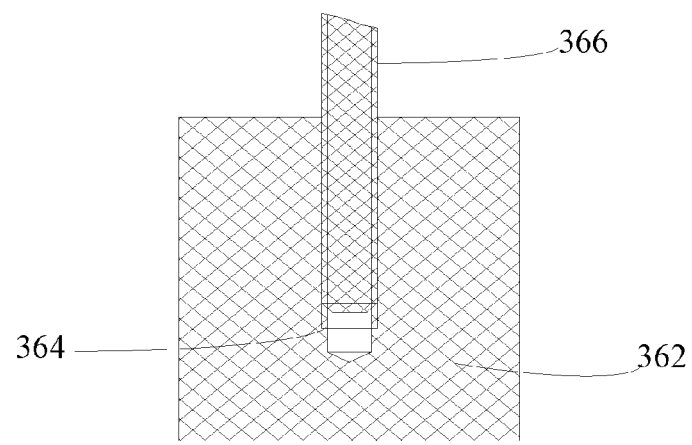
FIG. 12 is a connection sectional view of a sensor of a mower of a seventh embodiment.

Reference is made to FIG. 12, which is a sectional view of connection of a sensor 362 of an automatic mower of the present embodiment.

In the present embodiment, the automatic mower comprises a shell and a sensing component (not shown), and their arrangement and connecting relationship can refer to the sixth embodiment.

As shown in FIG. 12, the sensing component of the present embodiment further comprises a sensor connecting rod (not shown), the sensor 362 is disposed on the sensor connecting rod, the sensor 362 and the sensor connecting rod are in threaded connection, and the sensor 363 and the sensor connecting rod can be in an adjustable connecting manner.

In the present embodiment, the sensor connecting rod is provided with an extending end (not shown) facing to the working surface, internal threads 364 are disposed in the sensor 362, one end of the extending end close to the working surface is provided with a height adjusting stud 366, the internal threads 364 and the height adjusting stud 366 are adapted, the sensor 362 can be connected to the height adjusting stud 366 through the internal threads 364, and a matching and connecting length of the internal threads 364 and the height adjusting stud 366 can be adjusted.

It should be noted that it is not limited thereto in other embodiments, the height adjusting stud 366 can be disposed outside the sensor 362, the extending end is provided with internal threads 364, and the connection between the sensor 362 and the sensor connecting rod as well as relative height adjustment can also be realized.

Thus, when a user does not adjust the height of the sensing component, the height of the sensor 362 relative to the working surface can still be adjusted by a matching and connecting length of the internal threads 364 and the height adjusting stud 366 and further, the manual adjustment of the height of the sensor 362 is realized.

A specific operation method is: the user sleeves the sensor 362 on the height adjusting stud 366, such that the internal threads 364 of the sensor 362 are matched and connected with the height adjusting stud 366, if the sensor 362 is rotated counterclockwise from bottom to top, then the sensor 362 can be ascended relative to the working surface, and if the sensor 362 is rotated clockwise from top to bottom, then the sensor 362 can be descended relative to the working surface.

The automatic mower can comprise one or more sensors 362. In the present embodiment, the automatic mower comprises four sensors 362 which are uniformly distribute on the sensor connecting rod in an equal-radius circumferential manner. In other embodiments, the quantity and location of the sensors 362 are not limited thereto, the quantity can be three, and the sensors are in triangular distribution. In the present embodiment, the height of the one or more sensors 362 relative to the vegetation can be pertinently adjusted after the height of the sensing component is integrally adjusted, such that the automatic mower can sense the vegetation in different areas and having different heights, and a vegetation recognizing range of the sensors 362 is expanded.

According to the automatic mower above, a plurality of sensors 362 are disposed, the vegetation recognizing range of the automatic mower can be expanded, the height of each sensor 362 relative to the working surface can be independently adjusted manually, such that different sensors 362 have different heights, the vegetation in different areas and having different heights can be recognized by making full use of the sensors 362, and working efficiency of the automatic mower is improved.

Eighth Embodiment

According to the automatic mower in the present embodiment, an adjusting component can be manually rotated to drive the rotary component to rotate, such that the sensing component is driven to move up and down relative to the working surface.

Figure 13:
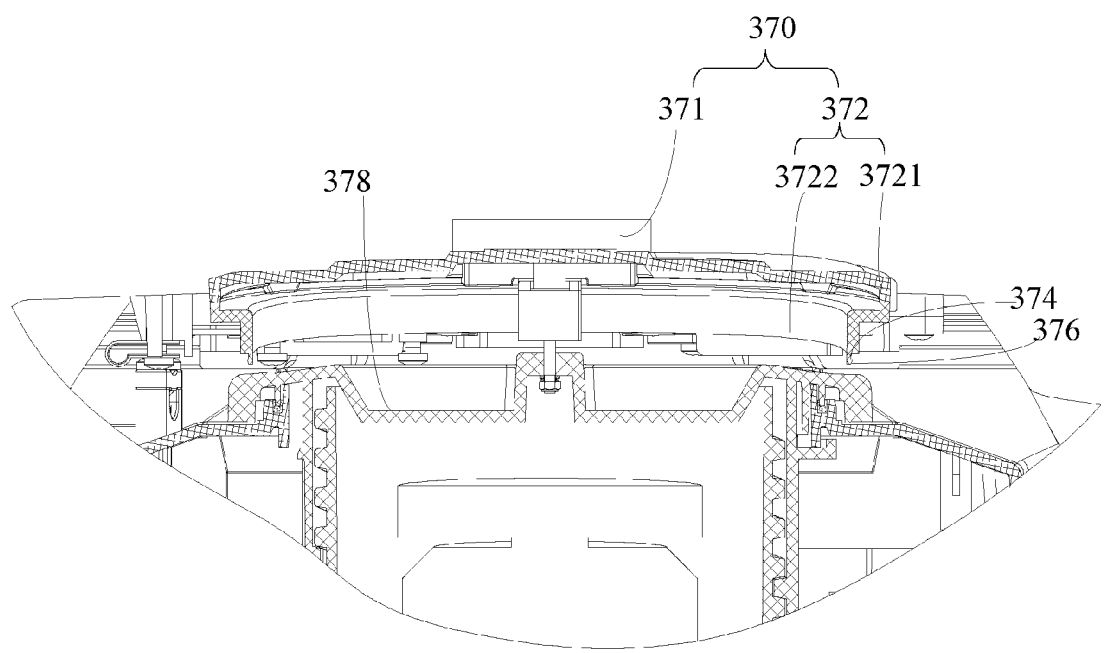
FIG. 13 is a sectional view of an adjusting knob and a locking device of a mower of an eighth embodiment.

Reference is made to FIG. 13, which is a sectional view of an adjusting knob 371 and a locking device 372 of the automatic mower of the present embodiment.

In the present embodiment, the automatic mower comprises a shell, a sensing component (not shown) and a rotating component 378, and their arrangement and location relationships can refer to the sixth embodiment.

As shown in FIG. 13, the automatic mower of the present embodiment comprises an adjusting component 370, disposed at one side of the rotary component 378 away from the working surface, the adjusting component 370 comprises an adjusting knob 371 and a locking structure 372, wherein the adjusting knob 371 can rotate and can move up and down, the locking structure 372 is disposed between the adjusting knob 371 and the rotary component 378 and can rotate along with rotation of the adjusting knob 371, and when the adjusting knob 371 is pressed down, the locking structure 372 is configured to fixedly connect the rotary component 378.

In the present embodiment, the adjusting knob 371 can be pressed down or reset along a direction vertical to the working surface. In the present embodiment, the locking structure 372 comprises a first connector 3721 and a second connector 3722, the first connector 3721 is connected to the adjusting knob 371, the second connector 3722 is connected to the rotary component 378, the first connector 3721 and the second connector 3722 are adaptive to each other, and when the adjusting knob 371 is pressed down, the first connector 3721 and the second connector 3722 are fixedly connected together.

In the present embodiment, both ends of the first connector 3721 facing to the second connector 3722 are provide with projecting hooks 374, hook grooves 376 are disposed in corresponding two ends on the second connector 3722, the projecting hooks 374 and the hook grooves 376 are adaptive to each other, when the height adjusting knob is pressed down, the projecting hooks 374 and the hook grooves 376 are fixedly connected together to realize that the first connector 3721 and the second connector 3722 are fixedly connected together, such that the adjusting knob 371 and the rotary component 378 are fixedly connected together.

When the user presses the adjusting knob 371 down, the adjusting knob 371 and the rotary component 378 are locked and fixedly connected together, such that the adjusting knob 371 is rotated to drive the rotary component 378 to rotate, the rotary component 378 drives the sensor (not shown) to upwards move in a direction vertical to the working surface by rotating and driving the sensing component (not shown) to move up and down, such that the height from the sensor to the working surface can be adjusted.

Thus, when the height of the sensing component needs to be manually adjusted, the user can manually adjust the sensing component to move up and down by the adjusting knob 371 and the locking structure 372, and further the height from the sensor to the vegetation can be adjusted.

Ninth Embodiment

In the present embodiment, a cam principle is used to realize adjustment of the height of the sensor relative to the working surface.

Figure 14:
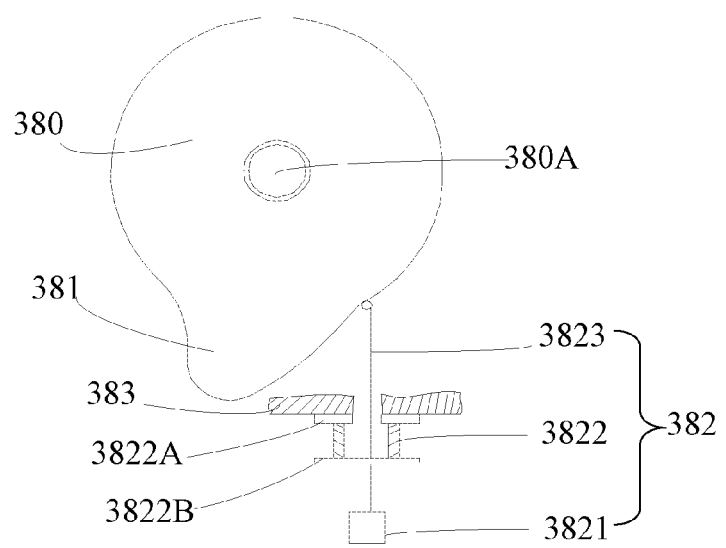
FIG. 14 is a connection schematic diagram of a cam and a sensing component of a mower of a ninth embodiment.

Reference is made to FIG. 14, which is a connecting schematic diagram of a cam 380 and a sensing component 382 of an automatic mower of the present embodiment.

In the present embodiment, the automatic mower comprises a shell 383 and a sensing component 382.

The automatic mower also comprises a cam motor (not shown) and a cam 380, the cam motor is fixed on a machine body 383, an output shaft of the cam motor is connected to a rotary shaft 380A of the cam 380, the rotary shaft 380A of the cam 380 is parallel with the working surface, the cam 380 comprises a projecting part 381 facing to the working surface, and the projecting part 381 can swing around the rotary shaft 380A of the cam 380 to swing to the working surface in a reciprocated manner.

The sensing component 382 also comprises a first elastic structure 3822 and a connecting rod 3823, the first elastic structure 3822 is vertical to the working surface and comprises a fixing end 3822A and a movable end 3822B, the fixing end 3822A is fixed on the machine body 383, the movable end 3822B moves up and down relative to the working surface, and the first elastic structure 3822 is configured to limit the sensing component 382 in a preset range. The connecting rod 3823 is vertical to the working surface, the middle of the connecting rod 3823 is connected to the movable end 3822B, one end of the connecting rod 3823 is connected to the sensor, the other end of the connecting rod abuts against the projecting part 381, and the reciprocated swing of the projecting part 381 drives the connecting rod 3823 to move up and down relative to the working surface.

Thus, the cam 380 is a driving part, and the sensing component 382 is a driven part of the cam 380. The cam motor drives the cam 380 to swing in a reciprocated manner, in the present embodiment, the cam motor drives the cam 380 to swing along the rotary shaft clockwise or counterclockwise, and further the projecting part 381 swings clockwise or counterclockwise towards the working surface in a reciprocated manner around the rotary shaft 380A of the cam 380. The connecting rod 3823 of the sensing component 382 abuts against the projecting part 381, and when the projecting part 381 swings in a reciprocated manner toward the working surface, the connecting rod 3823 is driven to move up and down.

The movable end 3822B of the first elastic structure 3822 in the present embodiment approaches to the working surface, and the fixing end 3822A of the first elastic structure 3822 is located above the movable end 3822B. Since the fixing end 3822A of the first elastic structure 3822 is fixed on the shell 383, the movable end 3822B is connected to the connecting rod 3823, when the projecting part 381 swings counterclockwise, the projecting part 381 drives the connecting rod 3823 to move downward, the connecting rod 3823 drives the movable end 3822B to move downwards, and the movable end 3822B stretches the first elastic structure 3822 and further drives the sensor to move downward. When the projecting part 381 swings clockwise, the first elastic structure 3822 is rebounded to drive the connecting rod 3823 to move upwards, so as to drive the sensor to move upwards. Thus, a rotary direction of the cam 380 can be adjusted by the cam motor according to a height of vegetation, such that the height from the sensor to the working surface can be correspondingly adjusted to adapt to cutting of the vegetation of different heights.

Tenth Embodiment

In the present embodiment, a height of the sensor relative to the working surface can be adjusted by using an elastic height follow-up structure.

Figure 15:
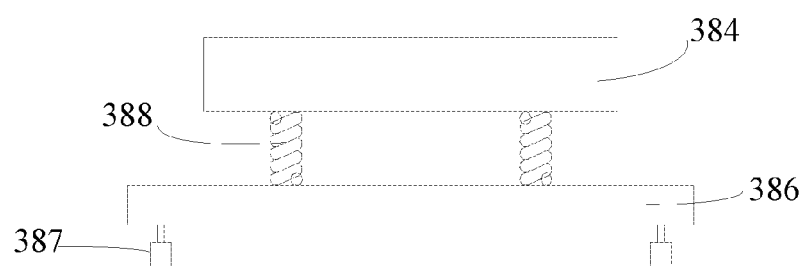
FIG. 15 is a connection schematic diagram of a second elastic structure and a sensing component of a mower of a tenth embodiment.

Reference is made to FIG. 15, which is a connecting schematic diagram of a second elastic structure 388 and a sensing component 386 of an automatic mower of the present embodiment.

In the present embodiment, the automatic mower comprises a shell 384 and a sensing component 386. The sensing component 386 is disposed on the shell 384, the sensing component 386 comprises a sensor (not shown), and the height of the sensor relative to the working surface is adjustable.

The automatic mower also comprises a second elastic structure 388, and the sensing component 386 is connected to the shell 384 through the second elastic structure 388. The second elastic structure 388 is vertical to the working surface, and is telescopic in a direction vertical to the working surface. When the automatic mower is not in work, the second elastic structure 388 is in an original state. In the present embodiment, the second elastic structure 388 is a spring.

In the present embodiment, the working surface is the ground, when vegetation is higher and touches the sensing component 386, the vegetation will transfer an upward force to the sensing component 386 and overcomes the gravity of the sensing component 386, at this point, the sensing component 386 compresses the second elastic structure 388, and meanwhile, the sensing component 386 moves upwards to drive the sensor to move upward. When the automatic mower advances to an area where the vegetation is shorter, the second elastic structure 388 extends under an action of gravity per se to drive the sensing component 386 to approach to the vegetation. Thus, the vegetation is effectively sensed, and is conveniently cut by the automatic mower.

It should be noted that in other embodiments, the stretching and drawing back of the second elastic structure 388 is not limited to this method, and can be controlled by an external force, so as to realize the adjustment of different heights of the sensing component 386 relative to the working surface.

In one of the embodiments, the second elastic structure is a torsional spring, which can be twisted at a preset angle, when the sensing component touches the vegetation at any angle, the vegetation gives a force of corresponding angle to the sensing component, since the sensing component is connected to the torsional spring, the torsional spring is twisted for a corresponding angle, and thus the adjustment of different degrees of freedom of the sensing component relative to the shell can be realized.

Eleventh Embodiment

The present embodiment realizes the height adjustment of a sensor 394C relative working surface by adopting a guide rail type height follow-up structure.

Figure 16:
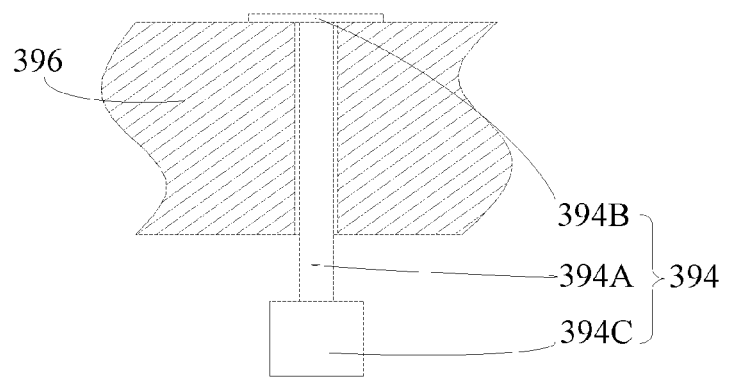
FIG. 16 is a schematic diagram of a sensing component of a mower of an eleventh embodiment.

Reference is made to FIG. 16, which is a schematic diagram of a sensing component 394 of an automatic mower of the present embodiment.

In the present embodiment, the automatic mower comprises a shell (not shown) and a sensing component 394. The sensing component 394 is disposed on the shell and comprises a sensor 394C, of which a height relative to the working surface is adjustable, and a probe of the sensor 394C faces to the working surface, and is configured to sense the vegetation.

The automatic mower also comprises a fixing plate 396, the fixing plate 396 is fixed on the shell and is provided with a through hole (not shown) vertical to the working surface, and the fixing plate 396 is configured to dispose the sensing component 394. The sensing component 394 also comprises a movable rod 394A and a limiting block 394B, the movable rod 394A penetrates through the through hole, the movable rod 394A reciprocates in the through hole relative to the working surface, the limiting block 394B is disposed at one end of the movable rod 394A away from the working surface, the sensor 394C is disposed at the other end of the movable rod 394A, and the limiting block 394B and the sensor 394C limit the movable rod 394A to move in the through hole of the fixing plate 396.

Thus, the movable rod 394A reciprocates in the through hole and moves in a preset range to drive the sensor 394C to move up and down relative to the working surface. When the vegetation is higher, the vegetation is pushed up by the sensor 394C, and the sensor 394C moves upwards together with the movable rod 394A. When the vegetation is shorter, the sensor 394C and the movable rod 394A are vertical to the vegetation due to a gravity action, and the size of the limiting block 394B is larger than that of the through hole to prevent the movable rod 394A from being separated from the fixing plate 396. According to the automatic mower, the height of the sensing component 394 can be freely adjusted along with the height of the vegetation, and the vegetation can be effectively recognized and cut.

It should be noted that in other embodiments, the up-down movement of the movable rod 394A in the through hole can be controlled by other external forces to realize the adjusting of different heights of the sensor 394C relative to the working surface.

In addition, therefore, it is necessary to design a control method for a height of a sensor specific to the problem that a sensor is fixed on the shell and a height cannot be adjusted. The height of the sensor of an automatic mower relative to the working surface can be adjusted, the misjudgment that the machine does not cut the grassland is reduced, and the problem of "short grass siege" is avoided, such that a vegetation trimming effect is ideal and working efficiency is improved.

Figure 17:
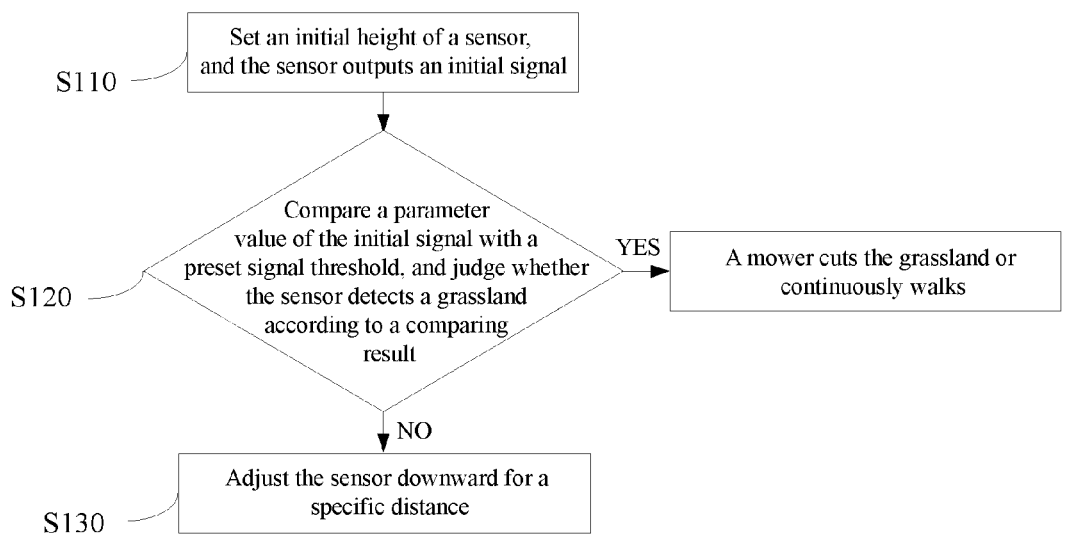
FIG. 17 is a flow schematic diagram of a control method for a height of a sensor of one embodiment.

Reference is made to FIG. 17, which is a flow schematic diagram of a control method for a height of a sensor of the present embodiment. As shown in FIG. 17, the control method for a height of a sensor is used for controlling a height of a sensor of the mower according to any one of the embodiments above and comprises the steps:

Step S110, setting an initial height of the sensor, the sensor outputting an initial signal.

Specifically, according to the initial signal output by the sensor, the automatic mower can judge whether grass is recognized or not to execute corresponding operation. The initial signal is a square wave signal, and the automatic mower can judge a vegetation recognizing condition according to related parameters of the square wave signal.

Step S120, comparing a parameter value of the initial signal with a preset threshold, judging whether the sensor detects vegetation according to a comparing result, if yes, enabling the mower to cut the vegetation or continuously walk, and if not, adjusting the sensor downwards for a specific distance.

Specifically, if the comparing result displays that the sensor detects the vegetation, then it is indicated that the current automatic mower is in the working area. The automatic mower judges whether the vegetation needs to be cut according to a current height of the sensor, and if the vegetation needs to be cut, the automatic mower executes the cutting operation. If the vegetation does not need to be cut, the automatic mower judges that the current vegetation area is a working area, and can continuously walk. If the comparing result displays that the sensor detects no vegetation, then the automatic mower adjusts the sensor downwards for a certain distance. In the present embodiment, the specific distance is set to be 0.5 cm in advance, and if the comparing result displays that the sensor detects no vegetation, then the sensor is descended by 0.5 cm.

According to the control method for a height of a sensor, the mower can judge whether the sensor detects the vegetation according to an output signal of the sensor, and the automatic mower can adjust the height of the sensor according to a detecting condition. When the sensor detects the vegetation, the automatic mower executes an operation of cutting the vegetation of continuously walks; and when the sensor displays that no vegetation is detected, the automatic mower reduces the height of the sensor and continues to detect. Thus, when recognizing the vegetation, the mower will not misjudge because of short grass, accuracy of vegetation recognition is improved, a cutting effect is better and cutting efficiency is higher.

In one of the embodiments, the step S120 further comprises: comparing a frequency value of the initial signal and a preset frequency threshold, judging whether the frequency value of the initial signal is smaller than the frequency threshold, if yes, indicating that the sensor detects the vegetation, and if not, indicating that the sensor does not detect the vegetation.

Specifically, an output signal of the sensor is the frequency signal, and the sensor presets the frequency threshold. If the sensor does not detect the grass, the frequency value is larger; and if the sensor detects the vegetation, the frequency value is smaller. If the frequency value of the initial signal is smaller than the frequency threshold, then it is indicated that the sensor detects the vegetation area. If the frequency value of the initial signal is not small than the frequency threshold, then it is indicated that the sensor detects no vegetation area. Thus, the automatic mower can judge whether the sensor recognizes the grass according to the frequency value output by the sensor, and accuracy and convenience are realized.

Figure 18:
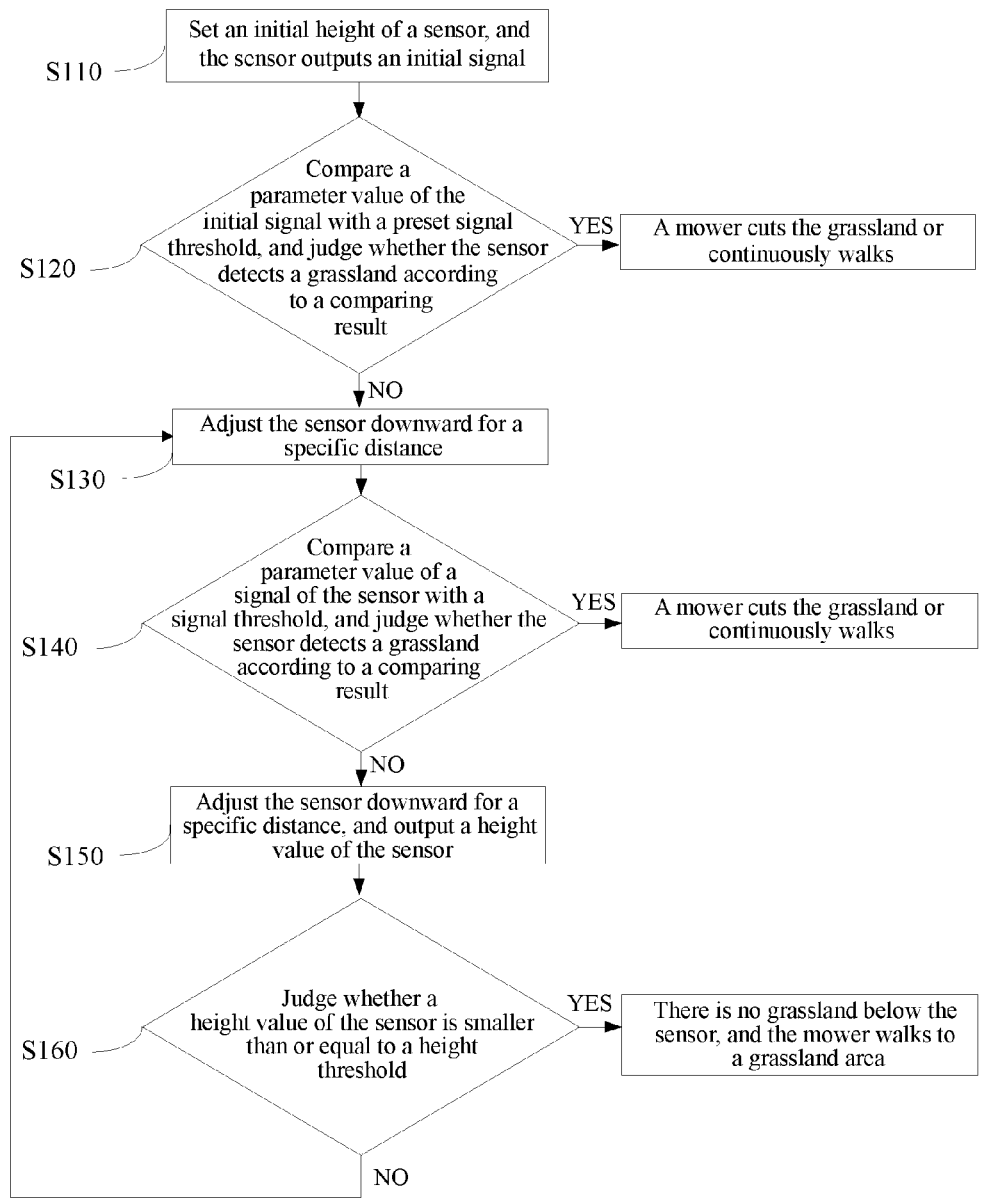
FIG. 18 is a flow schematic diagram of a control method for a height of a sensor of another embodiment.

Reference is made to FIG. 18, which is a flow schematic diagram of a control method for a height of a sensor of another embodiment. In the present embodiment, the method, after the step of adjusting the sensor downwards for a specific distance, further comprises:

Step S140, comparing a parameter value of a signal of the sensor and the parameter threshold, judging whether the sensor detects the vegetation according to a comparing result, if yes, enabling the mower to cut the vegetation or continuously walk, and if not, adjusting the sensor downwards for a specific distance and outputting a height value of the sensor.

In the present embodiment, the signal of the sensor is a square wave signal. The parameter value of the signal and the parameter threshold are parameters of the same type, for example, are both of a frequency value or level value, and have comparability. The automatic mower can judge whether the vegetation is detected by a comparing result. In the present embodiment, if the comparing result displays that the sensor does not detect the vegetation, then the sensor is descended for 0.5 cm. In addition, a height value of the sensor at this point is also output.

Step S160, judging whether a height value of the sensor is smaller than or equal to a height threshold, if yes, indicating that the mower walks to a vegetation region and if not, adjusting the sensor downwards for a specific distance.

Specifically, the automatic mower presets a height threshold of the sensor, that is, a minimal height of the vegetation detected by the sensor. If the height value of the sensor is smaller than or equal to the height threshold, then it is indicated that the sensor has been descended to be or to be lower than the minimal height, and it is further indicated that the area below the sensor is a nonworking area of the automatic mower, at this point, the automatic mower controls the sensor to walk to the working area and continuously detect and cut the vegetation. If the height value of the sensor is still larger than the height threshold, the height of the sensor is descended again, whether the vegetation exists below the sensor is continued to be judged, and the automatic mower executes the operation of corresponding steps according to a judging result. Thus, the automatic mower can more accurately recognize a vegetation area and a non-vegetation area.

In one of the embodiments, the step S140 further comprises a frequency value of the signal of the sensor and a preset frequency threshold, judging whether the frequency value of the signal of the sensor is smaller than the frequency threshold, if yes, indicating that the sensor detects the vegetation and the if not, indicating the sensor detects no vegetation.

Specifically, the signal of the sensor is a frequency signal, and the sensor presets the frequency threshold. If the frequency value of the signal of the sensor is smaller than the frequency threshold, then it is indicated that the sensor detects the vegetation area. If the frequency value of the signal of the sensor is not smaller than the frequency threshold, then it is indicated that the sensor detects no vegetation area. Thus, the automatic mower can judge whether the sensor recognizes the vegetation according to the frequency value output by the sensor and accuracy and convenience are realized.

In other embodiments of the present invention, probe comprises at least two polar plates, which are respectively connected to a control module electrically, and the polar plates have different potentials. Specifically, the polar plate comprises a shielding side, which is back to the surface below the automatic mower and is provided with a shielding layer.

Twelfth Embodiment

Figure 19:
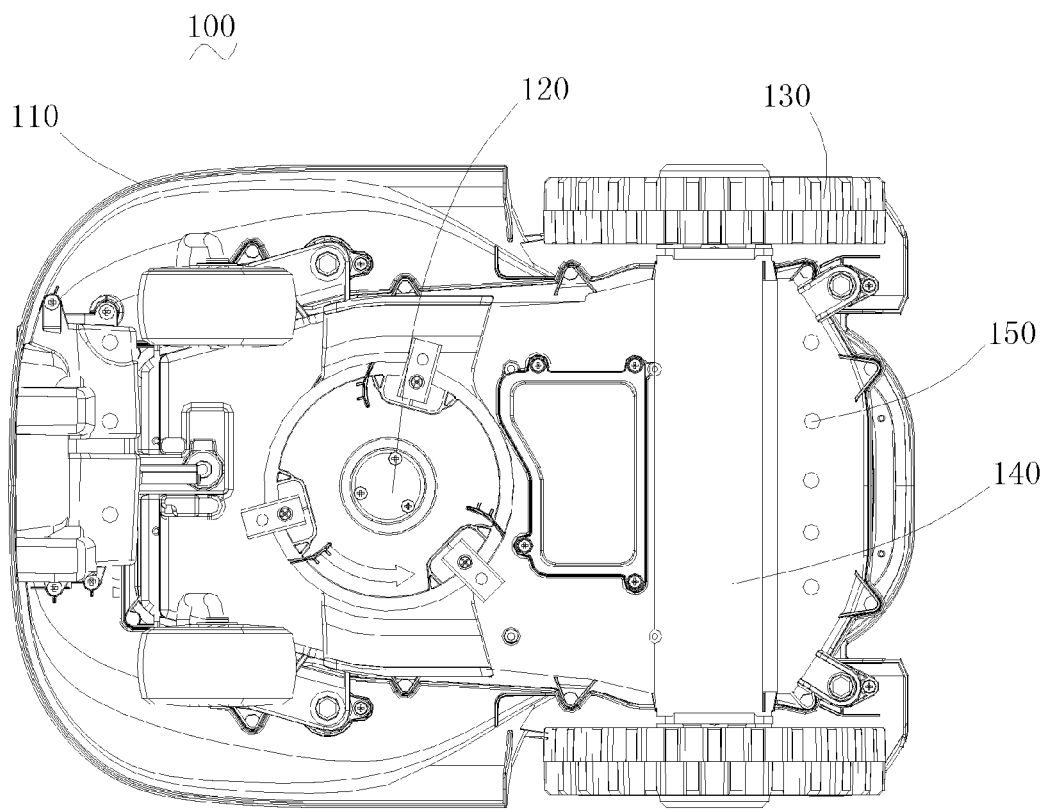
FIG. 19 is a schematic diagram of a mower of a twelfth embodiment.

Reference is made of FIG. 19, an automatic mower 100 comprises a shell 110, a cutting module 120, a moving module 130 and a control module, wherein the control module is configured to control the cutting module 120 and the moving module 130 to work. In order to reduce idling of the automatic mower and improve working efficiency, the automatic mower 100 is further provided with capacitance sensors 150 (short for sensors 150 hereinafter) on both sides of the cutting module 120, and the control module comprises a signal processing circuit 160 connected to the sensor 150.

Figure 20:
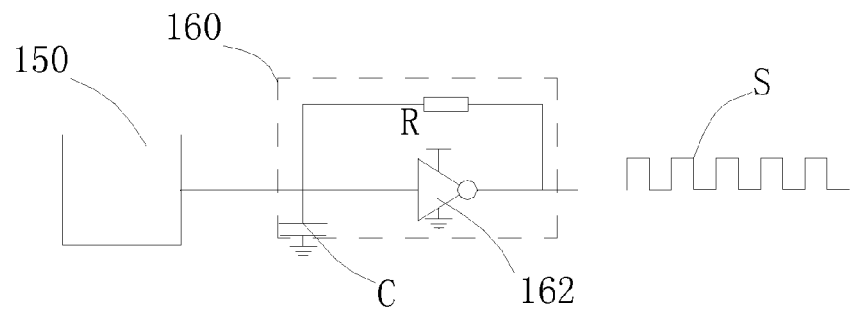
FIG. 20 is a principle diagram of a capacitance sensor of the twelfth embodiment.

Reference is made to FIG. 20, the sensor 150 judges a grass height, a grassland or non-grassland by adopting a capacitance principle. The capacitance of the sensor 150 in FIG. 20 will be changed when there is grass or not, such that an output signal S of the signal processing circuit 160 is changed. In FIG. 20, the signal processing circuit 160 contains a schmitt trigger 162, when the capacitance value of the sensor 150 is changed, an oscillation frequency of the output signal S of the schmitt trigger 162 will be changed, an MCU of the control module recognizes the change of the capacitance of the sensor 150 by reading a change of the signal frequency, so as to realize recognition on the grassland, non-grassland or the grass height, and a working command is sent to the cutting module 120 and the moving module 130 according to setting.

FIG. 20 is merely a principle diagram of a capacitance sensor 150, which shows a change of an oscillation frequency of the output signal S of the schmitt trigger 162 in the signal processing circuit 160 through capacitance change. But the capacitance change can be certainly converted into a voltage or current change through a different signal processing circuit and is then recorded and judged, and the purpose of recognizing the capacitance change can still be achieved.

Figure 21:
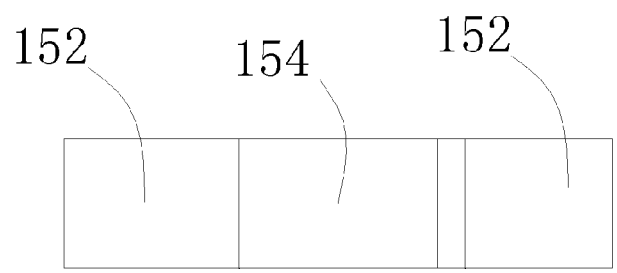
FIG. 21 is a schematic diagram of the capacitance sensor of the twelfth embodiment.
Figure 22:
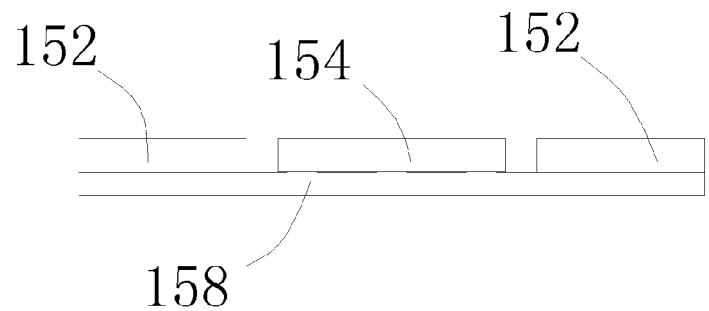
FIG. 22 is a schematic top view of the capacitance sensor of the twelfth embodiment.
Figure 23:
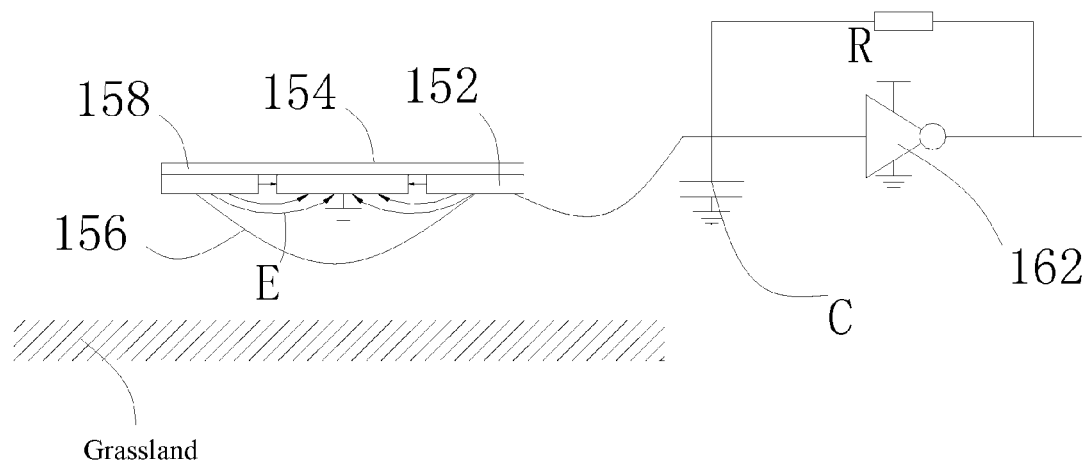
FIG. 23 is a schematic side view of the capacitance sensor of the twelfth embodiment.

Reference is made to FIGS. 21-23, the sensor 150 comprises three polar plates located on a same plane, including a first polar plate 152, a second polar plate 154 and a first polar plate 152 from left to right. The three polar plates are all made of a conductive metal material, and two first polar plates 152 are disposed and are respectively located on both sides of the second polar plate 154, and are connected by a lead 156. Thus, an electric field E is formed on left and right both sides of the second polar plate 154, and a larger sensing area is formed. Of course, one first polar plate 152 and one second polar plate 154 can be disposed and are disposed on the same plane in parallel.

The signal processing circuit 160 has an input end and an output end, wherein the first polar plate 152 is connected to an input end of the signal processing circuit 160, and the second polar plate 154 is connected to a common grounding end of the signal processing circuit 160, such that a capacitance is formed between the first polar plate 152 and the second polar plate 154. Specific to the present embodiment, the first polar plate 152 is connected to the input end of the schmitt trigger 162, and the second polar plate 154 is connected to a zero potential of the signal processing circuit 160

Figure 24:
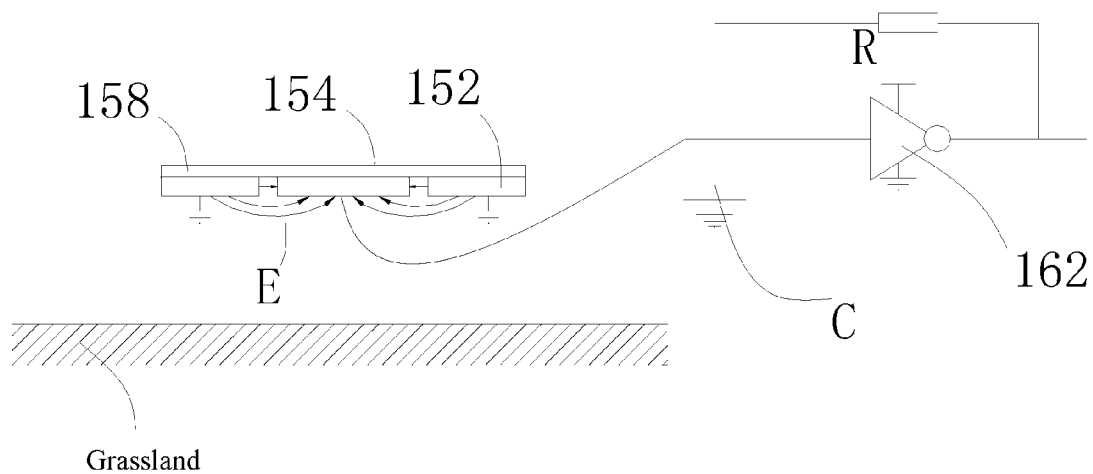
FIG. 24 is a schematic diagram of another connecting manner of the capacitance sensor of the twelfth embodiment.

Reference is made to FIG. 24, which shows another connecting manner between the sensor 150 and the signal processing circuit 160, wherein the first polar plate 152 is connected to a common grounding end of the signal processing circuit 160, and the second polar plate 154 is connected to an input end of the signal processing circuit 160.

According to a calculation formula C=(εS)/d of a parallel plate capacitance, wherein ε is a medium dielectric constant between two polar plates, S is polar plate direct facing area, and d is polar plate interval; and the size of C can be changed by adjusting ε, S or d. Therefore, when the grass height is changed, a medium change nearby the first polar plate 152 and the second polar plate 154 is caused, further a capacitance sensor is caused, i.e., a sensing function is realized.

When the control module judges that the grass height is larger than a preset height according to the capacitance change, the control module controls the cutting mechanism to execute a cutting work. An output frequency of the capacitance sensor 150 and the grass height have a certain linear corresponding relationship. For example, it is set that the higher the grass is, the lower the output signal frequency of the signal processing circuit 160 is. Generally, the signal frequency can be set to be changed for about 1 Mhz, by setting parameters of a resistor R in the sensor, the output frequency can be enabled to be smaller than 1 Mhz when the grass below the sensor is higher than 4 cm, otherwise, f is larger than 1 Mhz. The control module recognizes such change, such that the cutting module 120 is driven mow the grass or not, and the moving module 130 is controlled to advance or retreat.

Further, the control module finishes recognition on the grassland and non-grassland according to the capacitance change. The reason is that the non-grassland is equivalent to that the grass height is zero, and when the change exceeds a preset change, it can be determined that the grass height is changed to zero from 4 cm, and the grassland can be judged.

The sensor 150 is mounted below the sensor 110 to detect the height of the grass in the working area. The sensor 150 also comprises a support plate 158 connected to the shell 110, and the first polar plate 152 and the second polar plate 154 are disposed on the support plate 158 in parallel.

The first polar plate 152 and the second polar plate 154 are both disposed on the sensor 152. Therefore, an electric field E formed between the first polar plate 152 and the second polar plate 154 is located below the first polar plate 152 and the second polar plate 154, faces to one side of the grassland and is closer to the grassland, and higher detection sensitivity is realized.

In other words, since the electric field is pressed to one side of the grassland, a change of grass height enables the capacitance change to be more obvious, and the detection to be more sensitive. For example, when the frequency is set to be changed for about 1 M, when the grass height below the sensor 150 is 4 cm and when the solution is adopted, the output frequency is 800 khz, and when a solution of an upward electric field is adopted, the output frequency is 900 khz, therefore, when the solution is adopted, the sensor is more sensitive in detection.

The first polar plate 152 and the second polar plate 154 are both disposed along a horizontal direction. When the automatic mower 100 works, the first polar plate 152 and the second polar plate 154 are flush with the grassland, and it is ensured that the sensed electric field is pressed down to one side of the grassland.

The sensor 150 on the shell 110 is set to be height-adjustable to adapt to requirements on cutting of lawns with different heights, match with adjustment of the signal processing circuit 160, and further ensure a detection sensitivity. For example, when 8 cm lawn needs to be preserved, if the location of the sensor 160 still stays at the location where the 4 cm lawn is detected, a difficulty may be increased to the adjustment of the signal processing circuit 160, or detection cannot even be performed, at this point, the height of the sensor 150 on the shell 100 can be adjusted at first.

Reference is made to FIG. 19, a plurality of sensors 150 are disposed at left and right both sides of the cutting module 120, i.e., the front and back two ends of the shell 110 respectively. When the automatic mower 100 works, these sensors 150 respectively form sensing areas in front of and behind the cutting module 120 in a width direction of the automatic mower 100. Since the first polar plate 152 and the second polar plate 154 are disposed on the same plane, when a plurality of sensors 150 are disposed, sensing areas of the sensors 105 can be jointed together to form a continuous sensing area. A width of the continuous sensing area is larger than or equal to a cutting diameter of the cutting module 120. Thus, it can be ensured that the grass in the cutting range can be detected, and a condition that the grass height of a local area is proper but the grass height in single areas is larger is avoided.

The sensors 150 are disposed on both sides of the cutting module 120, the sensor at the left side judges whether the cutting operation is required to be executed before mowing, and the sensor at the right side has a rechecking function, and judges whether cutting is complete or not.

Thirteenth Embodiment

Figure 25:
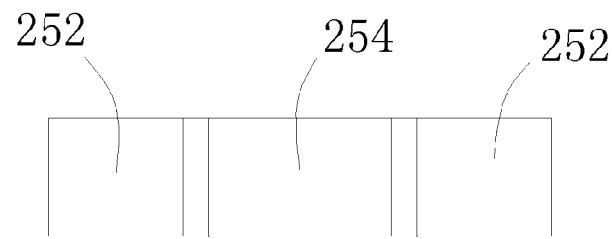
FIG. 25 is a schematic top view of a capacitance sensor of a thirteenth embodiment.
Figure 26:
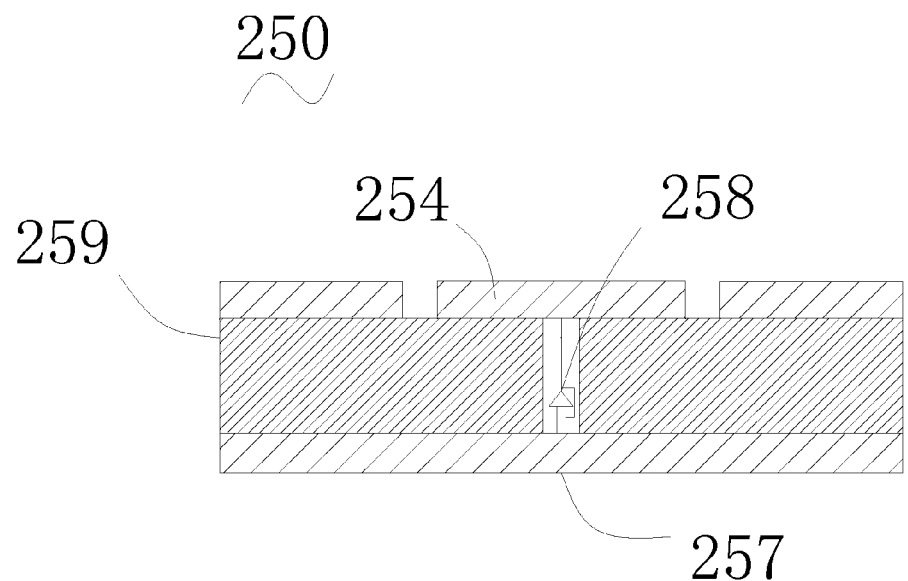
FIG. 26 is a schematic side view of the capacitance sensor of the thirteenth embodiment.
Figure 27:
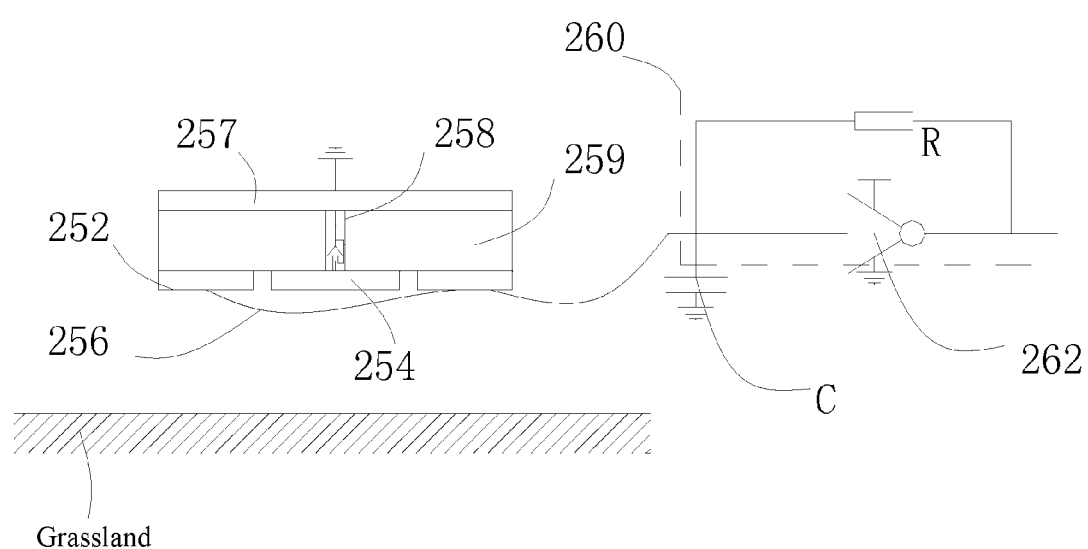
FIG. 27 is a schematic diagram of the capacitance sensor of the thirteenth embodiment.

Constitution of a capacitance sensor of the thirteenth embodiment is described in combination with FIGS. 25-27.

The sensor 250 comprises three polar plates made of a metal conductive material. The three polar plates are located on the same plane and form a downward electric field facing to the grassland. The two first polar plates 252 are located on both sides of the second polar plate 254, are connected together by a lead 256 and are connected to an input end of a schmitt trigger 262 in the signal processing circuit 260, and the second polar plate 254 is grounded.

The sensor 250 also comprises a shielding plate 257. The shielding plate 27 is disposed on the backs of the first polar plate 252 and the second polar plate 254, that is, one sides of the first polar plate 252 and the second polar plate 254 back to the grassland. The shielding plate 257 is connected to the second polar plate 254 through a voltage follower 258, and same potentials of the shielding plate 257 and the second polar plate 254 are realized, such that an interference caused by air change above the grassland is avoided. Meanwhile, the shielding plate also plays a role in pressing the electric field between the first polar plate 252 and the second polar plate 254 toward the grassland, and sensitivity of the capacitance sensor is further increased.

An insulation isolating plate 259 is disposed between the first polar plate 252 and the second polar plate 254 and the shielding plate, and a passage for disposing the voltage follower 258 is disposed in the insulation isolating plate 259.

Figure 28:
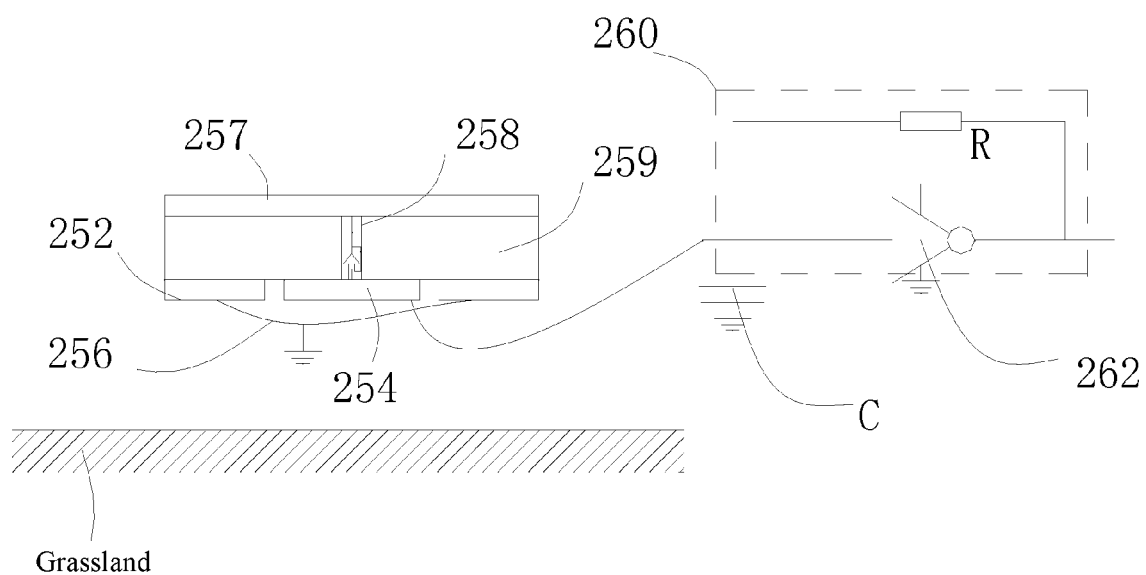
FIG. 28 is a schematic diagram of another connecting manner of the capacitance sensor of the thirteenth embodiment.

Reference is made to FIG. 28, which shows another connecting manner between the sensor 250 and the signal processing circuit 260. The two first polar plates 252 are connected to a common grounding end of the signal processing circuit 260, and the second polar plate 254 is connected to an input end of the signal processing circuit 260. In conclusion, the automatic mower 100 according to the present invention forms an electric field pressed toward the grassland on the sensor 150 or sensor 250, and therefore can quickly detect a height change of the grassland on the lawn to finish height recognition of the grassland and can further finish recognition on the grassland and the non-grassland.

The capacitance sensor according to the present invention can also be applied to a hand-push type mower or riding type mower for a user to ride.

In other embodiments of the present invention, the capacitance sensor comprises a connecting part, a connecting probe and a shell, the probe comprises a first rotary shaft, parallel with a working surface of the automatic mower, and the probe can rotate around the first rotary shaft relative to the connecting part. The connecting part comprises a second rotary shaft vertical to the working surface of the automatic mower, and the connecting part can rotate around the second rotary shaft relative to the shell, such that the probe rotates around the second rotary shaft. Specifically, the probe is an idler wheel, and the first rotary shaft is a wheel axle of the idler wheel. Specifically, the idler wheel is a universal wheel.

Fourteenth Embodiment

Figure 29:
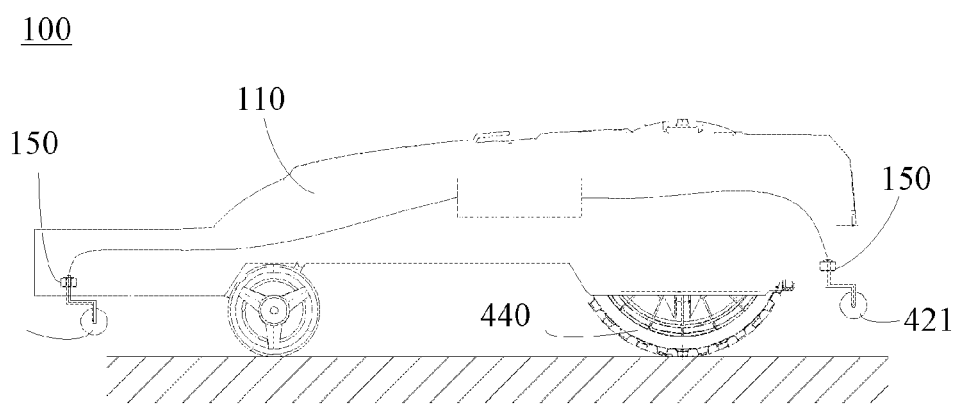
FIG. 29 is a schematic diagram of a mower of a fourteenth embodiment.
Figure 30:
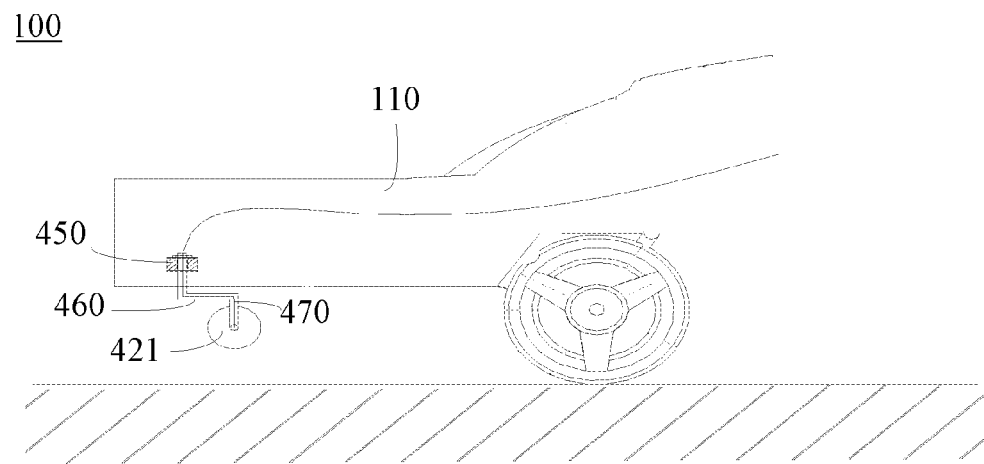
FIG. 30 is a connecting schematic diagram of an idler wheel of the mower as shown in FIG. 29.
Figure 31:
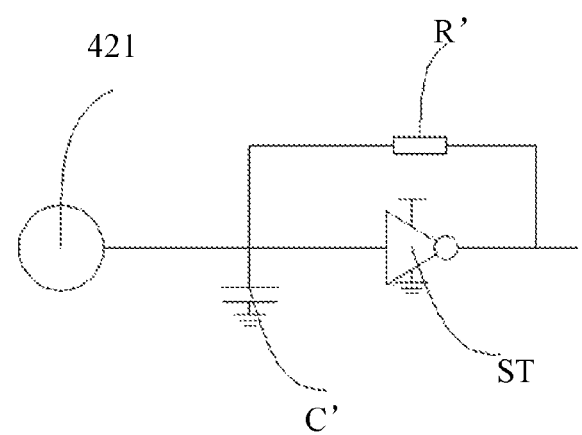
FIG. 31 is a schematic diagram of a signal processing circuit of the mower as shown in FIG. 29.

Reference is made to FIGS. 29-31, FIG. 29 is a schematic diagram of an automatic mower 100 of the present embodiment; FIG. 30 is a connecting schematic diagram of an idler wheel of the automatic mower as shown in FIG. 29; and FIG. 31 is a schematic diagram of a signal processing circuit of the automatic mower as shown in FIG. 29.

As shown in FIG. 29, an automatic mower 100 comprises a shell 110 and a capacitance sensor 150 disposed on the shell 110. The capacitance sensor 150 comprises an idler wheel 421, which is close to the bottom of the shell 110 and disposed at the bottom or periphery of the shell 110. The capacitance sensor 150 comprises at least one probe, disposed on the idler wheel 421 and configured to sense the grassland.

According to the automatic mower 100 above, since the probe is disposed on the idler wheel 421, if the idler wheel 421 makes a contact with the grassland, when the automatic mower advances, the idler wheel 421 rotates to walk, friction between the idler wheel 421 and the grassland is converted into rolling friction, and the friction between the probe and the grassland is reduced, such that an advancing resistance of the mower is reduced, energy consumption of the mower is reduced and mowing efficiency is improved.

As shown in FIG. 29, the automatic mower 100 can also comprise at least one main walking wheel 440, and the main walking wheel 440 is disposed on the bottom of the shell 110. Thus, the automatic mower 100 can freely walks on the grassland by depending on the main walking wheel 440, manual operation is greatly reduced, and the grassland can be conveniently quickly cut. The automatic mower 100 in the present embodiment comprises three main walking wheels 440, thus, the automatic mower 100 can be supported in a balanced manner and stably walks, but is not limited thereto in other embodiments.

The capacitance sensor 150 can be a capacitance humidity sensor, configured to sense a grassland condition. Thus, the capacitance sensor 150 can sense a specific state of the grassland according to a humidity condition of the grassland, and it is convenient for the automatic mower 100 to execute a cutting operation.

In one of the embodiments, the idler wheel 421 is of a dual-layer structure, including an inner layer and an outer layer, the polar plate is disposed on the inner layer and the outer layer is a protective layer. Thus, in an advancing process of the automatic mower 100, the protective layer outside the idler wheel 421 can protect the polar plate, and a service life of the probe is improved. Preferably, the inner layer is a metal layer, such that the sensing effect of the sensor is better.

In another embodiment, the outer layer protective layer can be made of plastic, thus, wear resistance of the idler wheel can be enhanced, and the polar plate disposed on the inner layer is better protected.

The idler wheel 421 is disposed on the bottom of the shell 110 in a suspending manner. Thus the lawn can be more precisely sensed. One or more idler wheels 421 are disposed. The quantity of the idler wheel 421 can be set as required to improve sensing efficiency. The present embodiment comprises two idler wheels 421, the two idler wheels 421 and the main walking wheel 440 are located on the bottom of the shell 110, the bottom of the main walking wheel 441 makes a contact with the ground, the two idler wheels 421 are respectively suspended in front of and/or behind an advancing direction of the main walking wheel 440, that is, when the grassland is shorter or the ground is flat, the bottoms of the two idler wheels 421 do not make a contact with the ground surface. In an advancing or retreating process of the automatic mower 100, when the grassland is higher or the grassland is uneven, the idler wheels 421 make a contact with the grassland, the idler wheels 421 advance or retreat as auxiliary wheels, friction with the grassland is avoided, a resistance from the grassland to the automatic mower 100 is reduced, and the automatic mower 100 can conveniently advance.

It should be noted that in other embodiments, the quantity of the idler wheels 421 is not limited thereto, and can be one or more. If one idler wheel 421 is disposed, while a sensing requirement on the grassland is met, cost can be saved. If a plurality of, for example, three or four, idler wheels 421 are disposed, they can be uniformly distributed, a grassland sensing range of the automatic mower 100 is increased, and the grassland is effectively curt.

As shown in FIG. 30, the automatic mower 100 also comprises a bearing 450 and a connecting shaft 460, the bearing 450 is disposed on the shell 110, and a central axis of the bearing 450 is vertical to the bottom of the shell 110. One end of the connecting shaft 460 is connected to the bearing 450, and the other end is connected to the idler wheel 421, and the idler wheel 421 and the connecting shaft 460 can rotate around the central axis of the bearing 450. Thus when the idler wheel 421 meets a higher grassland or obstacle at any angle in an advancing process, the idler wheel 421 can freely rotate around the central axis of the bearing 150, while the grassland is sensed, the grassland or obstacle can be avoided, a resistance of the grassland or obstacle to the idler wheel 421 can be reduced, an advancing resistance of the automatic mower 100 is further reduced, and mowing efficiency is improved. In the present embodiment, the connecting shaft 460 is in a bent-type, and an angle preset in advance is formed between a connecting line of both ends of the connecting shaft 460 and the central axis of the bearing 450. Thus, a rotary range of the idler wheel 421 around the central axis of the bearing 450 is larger, larger obstacle can be bypassed, and the automatic mower 100 is better assisted to advance.

The connecting shaft 460 is further provided with a lead track (not shown), a lead 470 penetrates through the lead track to connect the idler wheel 421 to the control module, thus signal transmission between the idler wheel 421 and the control module can be realized, and the automatic mower 100 can conveniently mow the grass.

In other embodiments, the idler wheel 421 can be a universal wheel. The universal wheel can freely rotate in a plane parallel with the grassland, thus, if the universal wheel meets the grassland at any angle in an advancing process, the probe located on the idler wheel 421 can recognize the grassland, and mowing efficiency is improved. Or if an obstacle is met, the idler wheel 421 can bypass the obstacle flexibly, a resistance from the obstacle to the idler wheel 421 is reduced, and further an advancing resistance of the automatic mower 100 is reduced.

The automatic mower 100 also comprises a control module, disposed on the shell 110, as shown in FIG. 31, the control module comprises a signal processing circuit, and an input end of the signal processing circuit is electrically connected to a probe of the capacitance sensor. The probe of the capacitance sensor comprises a pole piece, and the ground surface or the ground of the signal processing circuit serves as a reference pole piece of the capacitance sensor. By detecting a change of the capacitance between the probe and the ground surface, a grassland condition is judged. The signal processing circuit outputs square waves according to the signal transmitted by the capacitance sensor. When the probe senses the grassland, a dielectric constant between the probe and the ground surface is increased, the capacitance between the probe and the ground surface is increased, and the frequency of the square waves output by the signal processing circuit is reduced. When there is no grass, the dielectric constant between the probe and the ground surface is reduced, the capacitance between the probe and the ground surface is also reduced, and the frequency of the square waves output by the signal processing circuit is increased. Therefore, the control module can judge a grassland condition according to the frequency of the square waves output by the signal processing circuit, and a working state of mowing is controlled.

It should be noted that in other embodiments, the location of the signal processing circuit is not limited into the control module, and can also be contained in the capacitance sensor. In addition, the signal change of the signal processing circuit is not limited thereto, when the idler wheel 421 senses the grassland, the output signal of the signal processing circuit can also be a level change as long as it is indicated that the idler wheel 421 can sense the grassland.

Specifically, the signal processing circuit comprises a schmitt trigger ST, and an input end of the schmitt trigger ST is connected to the idler wheel 421. When the idler wheel 421 senses the grassland, an output signal of the schmitt trigger ST is changed to realize that the automatic mower 100 automatically recognizes the grassland. Further, the signal processing circuit also comprises a capacitor C' and a resistor R'. One end of the capacitor C' is connected to the input end of the schmitt trigger ST, and the other end is grounded. Both ends of the resistor R' are connected between the input end and output end of the schmitt trigger ST in parallel. If there is grass below the idler wheel 421 or the idler wheel 421 makes a contact with the grass, a change of the capacitance C' is caused, such that the output signal of the schmitt trigger ST is changed, grassland detection is realized, and the grassland can be effectively cut.

The present invention is not limited to listed specific embodiment structures, and structures based on a concept of the present invention all fall within a protective scope of the present invention.

What is claimed is:

1. A self-moving device, moving and working in a working area defined by a limit, and comprising:
   a shell, a moving module, a task executing module and a control module,
   the control module controlling the moving module to drive the self-moving device to move and controlling the task executing module to execute a work task;
   the self-moving device comprising at least one capacitance sensor, which is mounted to the shell and electrically connected to the control module and detects whether a surface below the self-moving device or in front of a moving direction is a surface to be processed,
   wherein the self-moving device is characterized in that the capacitance sensor comprises at least one probe, the probe comprises a probing surface located on the outer surface of the probe, and a conductivity of at least part of the probing surface is larger than or equal to $10^{-9}$ s/m.

2. The self-moving device according to claim 1, characterized in that the probing surface comprises a lower surface facing to the surface below the self-moving device, and a conductivity of the lower surface is larger than or equal to $10^{-9}$ s/m.

3. The self-moving device according to claim 1, characterized in that the capacitance sensor comprises a longitudinal axis extending downwards form the shell, the probing surface comprises a surrounding surface around the longitudinal axis, and a conductivity of the surrounding surface is larger than or equal to $10^{-9}$ s/m.

4. The self-moving device according to claim 1, characterized in that the probing surface comprises a side surface, vertical to a working surface of the self-moving device or inclined for a preset angle relative to the working surface of the self-moving device, and a conductivity of the side surface is larger than or equal to $10^{-9}$ s/m.

5. The self-moving device according to claim 1, characterized in that the probe comprises at least one polar plate electrically connected to the control module, a conductivity of the polar plate is larger than or equal to $10^{-9}$ s/m, and the probing surface comprises a surface of the polar plate.

6. The self-moving device according to claim 1, characterized in that the probe comprises at least one polar plate electrically connected to the control module and a cladding layer at least partially cladding the polar plate, a conductivity of an outer surface of the polar plate is larger than or equal to $10^{-9}$ s/m, and the probing surface comprises an outer surface of the cladding layer.

7. The self-moving device according to claim 6, characterized in that the cladding layer comprises an inner layer close to the polar plate and an outer layer away from the polar plate, a conductivity of the inner layer is smaller than or equal to 10−9 s/m, and a conductivity of the outer layer is larger than or equal to $10^{-9}$ s/m.

8. The self-moving device according to claim 7, characterized in that an interval between the polar plate and the outer layer of the cladding layer is smaller than or equal to a preset distance.

9. The self-moving device according to claim 2, characterized in that the control module comprises a signal processing circuit processing an electric signal input by the capacitance sensor and also comprises a protective circuit electrically connected to the capacitance sensor and the signal processing circuit, and when a value of the electric value input by the capacitance sensor is larger than or equal to a threshold, the protective circuit reduces the value of the electric value input by the capacitance sensor, such that the value of the electric value input to the signal processing circuit is kept in a preset range.

10. The self-moving device according to claim 1, characterized in that the probe comprises at least two polar plates electrically connected to the control module respectively, and the polar plates have different potentials.

11. The self-moving device according to claim 10, characterized in that the polar plate comprises a shielding side back to the surface below the self-moving device, and the shielding side is provided with a shielding layer.

12. The self-moving device according to claim 1, characterized in that the capacitance sensor comprises a connecting part connected to the probe and the shell, the probe comprises a first rotary shaft parallel with a working surface of the self-moving device, and the probe can rotate around the first rotary shaft relative to the connecting part.

13. The self-moving device according to claim 12, characterized in that the connecting part comprises a second rotary shaft vertical to the working surface of the self-moving device, and the connecting part can rotate around the second rotary shaft relative to the shell, such that the probe rotates around the second rotary shaft.

14. The self-moving device according to claim 12, characterized in that the probe is a wheel, and the first rotary shaft is a wheel axle of the wheel.

15. A control method for a self-moving device, wherein the self-moving device comprises at least one capacitance sensor for detecting whether a surface below the self-moving device or in front of a moving direction is a surface to be processed, the capacitance sensor comprises at least one probe, the probe comprises a probing surface located on the outer surface of the probe, and the control method for a self-moving device is characterized by comprising the following steps:
  providing the probing surface, part of which has a conductivity being larger than or equal to 10−9 s/m;
  judging whether the surface below the self-moving device or in front of a moving direction is a surface to be machined according to an electric signal output by the capacitance sensor;
  controlling the self-moving device to continuously move when the surface is judged to be a surface to be machined; and
  controlling the self-moving device to change a moving manner when the surface is judged not to be a surface to be machined.

* * * * *